United States Patent
Aubert et al.

(10) Patent No.: US 10,125,400 B2
(45) Date of Patent: Nov. 13, 2018

(54) METHOD FOR THE DIAGNOSIS OF ROSACEA

(71) Applicants: GALDERMA RESEARCH & DEVELOPMENT, Biot (FR); UNIVERSITE D'AIX-MARSEILLE, Marseilles (FR); CENTRE NATIONAL DE LA RECHERCHE SCIENTIFIQUE, Paris (FR)

(72) Inventors: Jérôme Aubert, Grasse (FR); Nathalia Murillo, Marseilles (FR); Didier Raoult, Marseilles (FR)

(73) Assignee: GALMERMA RESEARCH & DEVELOPMENT, Biot (FR)

(*) Notice: Subject to any disclaimer, the term of this patent is extended or adjusted under 35 U.S.C. 154(b) by 475 days.

(21) Appl. No.: 14/420,400

(22) PCT Filed: Aug. 8, 2013

(86) PCT No.: PCT/EP2013/066637
§ 371 (c)(1),
(2) Date: Feb. 9, 2015

(87) PCT Pub. No.: WO2014/023803
PCT Pub. Date: Feb. 13, 2014

(65) Prior Publication Data
US 2015/0307922 A1    Oct. 29, 2015

Related U.S. Application Data

(60) Provisional application No. 61/681,957, filed on Aug. 10, 2012, provisional application No. 61/740,997, filed on Dec. 21, 2012.

(51) Int. Cl.
| | | |
|---|---|---|
| *C12Q 1/68* | (2018.01) | |
| *C12Q 1/689* | (2018.01) | |
| *C12Q 1/6888* | (2018.01) | |
| *C12Q 1/6883* | (2018.01) | |

(52) U.S. Cl.
CPC ........... *C12Q 1/689* (2013.01); *C12Q 1/6883* (2013.01); *C12Q 1/6888* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2005/0048088 A1 | 3/2005 | Zulli et al. |
| 2007/0134276 A1 | 6/2007 | Menegatti et al. |
| 2008/0193393 A1 | 8/2008 | Dayan |
| 2009/0258065 A1 | 10/2009 | Baudonnet et al. |

OTHER PUBLICATIONS

Jansen et al. (Rosacea: classification and treatment, J R Soc Med. Mar. 1997; 90(3): 144-150).*
Moravvej et al. (Association of rosacea with demodicosis, Arch Iran Med. Apr. 2007;10(2):199-203).*
Grice et al. (A diversity profile of the human skin microbiota, Genome Res. Jul. 2008;18(7)1 043-50. doi: 10.1101/gr.075549.107. Epub May 23, 2008).*
Janda et al.(16S rRNA gene sequencing for bacterial identification in the diagnostic laboratory: pluses, perils, and pitfalls, J Clin Microbiol. Sep. 2007:45(9):2761-4. Epub Jul. 11, 2007).*
Woo et al. (Then and now: use of 16S rDNA gene sequencing for bacterial identification and discovery of novel bacteria in clinical microbiology laboratories, Clin Microbiol Infect. Oct. 2008;14(10):908-34).*
Lacey et al. (Mite-related bacterial antigens stimulate inflammatory cells in rosacea, Br J Dermatol. Sep. 2007;157(3):474-81. Epub Jun. 26, 2007).*
O'Reilly et al. (Positive correlation between serum immunoreactivity to Demodex-associated Bacillus proteins and erythematotelangiectatic rosacea, Br J Dermatol. Nov. 2012;167(5):1032-6. Epub Sep. 25, 2012).*
O'Reilly et al. (Demodex-associated bacterial proteins induce neutrophil activation, Br J Dermatol. Apr. 2012;166(4):753-60. Epub Mar. 2, 2012).*
Li et al. (Correlation between ocular Demodex infestation and serum immunoreactivity to Bacillus proteins in patients with Facial rosacea, Ophthalmology. May 2010;117(5):870-877.e1. Epub Jan. 15, 2010).*
Zhao et al. (Retrospective analysis of the association between Demodex infestation and rosacea, Arch Dermatol. Aug. 2010;146(8): 896-902).*
International Search Report dated Sep. 25, 2013 corresponding to International Patent Application No. PCT/EP2013/066637, 5 pages.
Lacey, N., et al. "Mite-related bacterial antigens stimulate inflammatory cells in rosacea," British Journal of Dermatology, vol. 157, No. 3, Jun. 26, 2007, pp. 474-481.
O'Reilly, N., et al. "Demodex-Associated Bacillus Proteins Induce an Aberrant Wound Healing Response in a Corneal Epithelial Cell Line: Possible Implications for Corneal Ulcer Formation in Ocular Rosacea," Investigative Ophthalmology & Visual Science, vol. 53, No. 6, May 31, 2012, pp. 3250-3259.
O'Reilly, N., et al., "Demodex-associated bacterial proteins induce neutrophil activation," British Journal of Dermatology, vol. 166, No. 4, Apr. 2, 2012, pp. 753-760.

(Continued)

*Primary Examiner* — Aaron A Priest
(74) *Attorney, Agent, or Firm* — Dentons US LLP

(57) ABSTRACT

A method of characterizing specific microbiota associated with *Demodex* mites from a rosacea patient is described. The method can include a step of realizing a biopsy on the patient and analyzing the microbiota based on a method of 16SrRNA sequencing or pyrosequencing. A method for the diagnosis of rosacea in a patient is also described. This method can include characterizing microbiota associated with *Demodex* mites in the patient. Also described, are methods of differentiating a subtype of rosacea in a patient with rosacea and methods of controlling and measuring an active agent's treatment effectiveness on rosacea.

20 Claims, 5 Drawing Sheets
Specification includes a Sequence Listing.

(56) References Cited

OTHER PUBLICATIONS

Lazaridou, E., et al., "The potential role of microorganisms in the development of rosacea," JDDG: Journal Der Deutschen Dermatologischen Gesellschaft, vol. 9, No. 1, Jan. 8, 2011, pp. 21-25.

Lee, S.H., et al. "The Relationship between Demodex and Ocular Discomfort," Investigative Ophthalmology & Visual Science, vol. 51, No. 6, Jun. 1, 2010, pp. 2906-2911.

Li, J., et al., "Correlation between Ocular Demodex Infestation and Serum Immunoreactivity to Bacillus Proteins in Patients with Facial Rosacea," Ophthalmology, J. B. Lippincott Co., Philadelphia, PA, US, vol. 117, No. 5, May 1, 2010, pp. 870-877.

Gerber, P.A., et al. "Rosacea: the Cytokine and Chemokine Network", Journal of Investigative Dermatology Symposium Proceedings, vol. 15, No. 1, Dec. 1, 2011, pp. 40-47.

De Rojas, M., et al., "Morphobiometrical and molecular study of two populations of Demodex folliculorum from humans," Parasitology Research; Founded as Zeitschrift Fur Parasitenkunde, Springer, Berlin, DE, vol. 110, No. 1, Jun. 7, 2011, pp. 227-233.

Scheinfeld, N., et al., "A Review of the Diagnosis and Treatment of Rosacea," Postgraduate Medicine, vol. 122, No. 1, Jan. 2010, pp. 139-143.

Jarmuda, S., et al., "Potential role of Demodex mites and bacteria in the induction of rosacea," Journal of Medical Microbiology, vol. 61, No. Pt 11, Aug. 29, 2012, pp. 1504-1510.

Murillo, N., et al., "Microbiota of Demodex mites differs between rosacea subjects and controls," Journal of Investigative Dermatology, Nature Publishing Group, GB, vol. 133, No. Suppl. 1, May 1, 2013, p. S193.

* cited by examiner

METHOD FOR THE DIAGNOSIS OF ROSACEA

CROSS-REFERENCE TO PRIOR APPLICATIONS

This application is a National Stage of PCT/EP2013/066637, filed Aug. 8, 2013, and designating the United States (published in English on Feb. 13, 2014, as WO 2014/023803 A1), which claims priority under 35 U.S.C. § 119 to U.S. Provisional Application No. 61/681,957, filed Aug. 10, 2012, and to U.S. Provisional Application No. 61/740,997, filed Dec. 21, 2012, each hereby expressly incorporated by reference in its entirety and each assigned to the assignee hereof.

FIELD OF THE INVENTION

The present invention relates to a method for the diagnosis of rosacea and a method to discriminate between subtypes of rosacea.

BACKGROUND OF THE INVENTION

Rosacea is a common, chronic and progressive inflammatory disease with skin features characterized by blushing and flushing, facial erythema, papules, pustules, telangiectasia and sometimes ocular lesions known as ocular rosacea. In severe cases, particularly in men, rhinophyma, or a bulbous enlargement of the nose, may occur. Rosacea develops over the course of several years with periods of exacerbation triggered by various stimuli such as temperature changes, alcohol, spicy foods, sun exposure and emotional factors.

The prevalence of rosacea in the European population ranges between 0.09 and 22%, with a peak age of onset between 25 and 70 and is much more common in people with a light complexion. It more particularly affects women although the condition is generally more severe in men. The prevalence of family histories of rosacea has been reported.

Four subtypes of rosacea have been defined according to the degree of primary features, such as vasomotor flushing, persistent erythema, papules and pustules, telangiectasias (Wilkin J et al., JAAD, 2002, 46: 584-587):

Erythematotelangiectatic rosacea (ERT) is mainly characterized by vasomotor flushing and persistent central facial erythema. Telangiectasias are commonly observed but are not essential for the diagnosis of this subtype. Central facial edema, burning or stinging sensations and rough, flaky skin are also symptoms that have sometimes been reported. A history of flushing as the only symptom is commonly found in people with erythematotelangiectatic rosacea.

Papulopustular rosacea (PPR) is characterized by persistent central facial erythema and transient crops of papules and/or pustules in the center of the face. However, the papules and pustules can also occur in periorificial regions, i.e., around the mouth, nose and eyes. The papulopustular subtype resembles acne vulgaris, but comedones are absent. Rosacea and acne may coexist in a same patient, in which case comedones may also be present alongside the papules and pustules suggestive of rosacea. People with papulopustular rosacea sometimes complain of a burning or stinging sensation. This subtype is often observed before or at the same time as ER (including the presence of telangiectasias). The telangiectasias may be obscured by the persistent erythema and the papules and pustules, but they tend to become more visible after successful treatments that cover up these features.

Phymatous rosacea is characterized by a thickening of the skin, irregular surface nodularities and swelling. The nose is most commonly affected but phymatous rosacea can also involve other areas such as the chin, the forehead, the cheeks and the ears. Patients with this subtype sometimes exhibit prominent, enlarged follicles in the affected areas as well as telangiectasias. This subtype often occurs before or at the same time as ER or PPR (including the presence of persistent erythema, telangiectasias, papules and pustules). In the case of rhinophyma, these additional stigmata may be particularly pronounced in the nasal region.

Ocular rosacea (or ophthalmic rosacea) exhibits symptoms restricted to the ocular area with blepharitis, conjunctivitis and keratitis. The diagnosis of ocular rosacea should be considered when a patient presents with one or more of the following ocular signs and symptoms: watery or bloodshot eyes (interpalpebral conjunctival hyperemia), foreign body sensation, burning or stinging, dry or itchy eyes, sensitivity to light, blurred vision, conjunctival telangiectasias or eyelid margin telangiectasias or erythema of the eyelid and periocular area.

The pathogenesis of this disease is still unknown and might differ according to subtypes. Many studies describe rosacea as a vascular system disorder related to UV exposure or an immune disorder with an increased expression of pattern recognition receptors, which triggers an exacerbated response to microorganisms such as *Demodex* mites.

The *Demodex* mites have been studied in rosacea patients to investigate their role in the pathogenesis of the disease. However, the importance of these mites remains controversial. Indeed, a small number of studies failed to demonstrate an increase in *Demodex* density in patients with rosacea. Moreover, culture-dependent studies do not allow for a consistent picture of the skin microbiota to be obtained.

Surprisingly, by conducting experiments and researches on *Demodex* mites, the inventors have demonstrated that the microbiota of *Demodex* mites differs between rosacea patients and control. Furthermore, the inventors have shown that the characterization of the specific microbiota associated with *Demodex* may be performed using a method of 16SrRNA sequencing. These results can be advantageously used for implementing a method for the diagnosis of rosacea.

SUMMARY OF THE INVENTION

The present invention provides a new method for diagnosing rosacea in a human subject, comprising the study of the microbiota associated with *Demodex* mites of the subject. According to the invention, the microbiota associated with *Demodex* mites may be analyzed for determining the prevalence of bacteria which are associated with rosacea condition. The method of the invention may be advantageously implemented to early diagnose rosacea, as well as to confirm or rule out a rosacea diagnostic. In addition, the invention provides means to discriminate between two subtypes of rosacea, i.e. between Erythematotelangiectatic rosacea and Papulopustular rosacea.

It is an object of the present invention to provide a method of characterizing specific microbiota associated with *Demodex* mites from a rosacea patient, the method comprising a step of realizing or providing a biopsy on the patient and analyzing the microbiota, in particular the microbiota associated with *Demodex* mites, based on a method of 16SrRNA sequencing or pyrosequencing.

It is a further object of the invention to provide a method for the diagnosis of rosacea in a patient, the method comprising characterizing microbiota associated with *Demodex* mites in the patient, using a method of 16SrRNA sequencing or pyrosequencing.

According to an embodiment, the prevalence of Gram negative bacteria in a biopsy of the patient is used as a diagnostic marker of rosacea.

Advantageously, the Gram negative bacteria are selected from the group consisting of *Bartonella* and *Escherichia coli*, preferably from the group consisting of *Bartonella Quintana* and *Escherichia coli*.

In a particular embodiment, the Gram negative bacteria is *Bartonella* in the erythematotelangiectatic rosacea (ETR) patient and/or the Gram negative bacteria is *Escherichia* in the papulopulstular rosacea (PPR) patient.

According to an embodiment of the invention, an increase of the prevalence of at least one bacterium selected from the group of Firmicutes, Actinobacteria and Proteobacteria, preferably from the group of Firmicutes and Proteobacteria, is a diagnostic marker of rosacea.

In an embodiment of the invention, the presence of at least one of the bacteria listed in Table 1, Table 2, Table 3 and/or Table 4 is a diagnostic marker of papulopustular rosacea (PPR) or erythematotelangiectatic rosacea (ETR).

Advantageously, the presence of two, preferably of three, more preferably of four, even more preferably of five bacteria listed in Table 1, Table 2, Table 3 and/or Table 4 is a diagnostic marker of papulopustular rosacea (PPR) or erythematotelangiectatic rosacea (ETR).

In a further embodiment of the invention, a decrease of the prevalence of Actinobacteria in the biopsy compared to a control is a diagnostic marker of papulopustular rosacea (PPR).

In an embodiment of the invention, the presence of at least one of the bacteria listed in Table 2 in the biopsy is a diagnostic marker of papulopustular rosacea (PPR).

Advantageously, the presence of two, preferably of three, more preferably of four, even more preferably of five bacteria listed in Table 2 in the biopsy is a diagnostic marker of papulopustular rosacea (PPR).

It is a further object of the invention to provide a method for the diagnosis of papulopustular rosacea in a patient, the method comprising characterizing Proteobacteria in the patient.

A further object of the invention relates to a method of differentiating a subtype of rosacea in a patient with rosacea, comprising a step of characterizing a microbiota associated with *Demodex* mites in a biopsy taken from the patient using a method of 16SrRNA sequencing or pyro sequencing.

Preferably, the subtype of rosacea is erythemato-telangiectatic rosacea or papulopulstular rosacea.

According to an embodiment, an increase of Proteobacteria and/or a decrease of Actinobacteria in the biopsy, compared to a control, is a diagnostic marker of papulopustular rosacea.

According to a particular embodiment, the presence in the biopsy of at least one of the bacteria listed in Table 1 is a diagnostic marker of erythematotelangiectatic rosacea (ETR) and/or the presence of at least one of the bacteria listed in Table 2 is a diagnostic marker of papulopustular rosacea (PPR).

Advantageously, the presence of two, preferably of three, more preferably of four, even more preferably of five bacteria listed in Table 1 in the biopsy is a diagnostic marker of erythematotelangiectatic rosacea (ETR).

Advantageously, the presence of two, preferably of three, more preferably of four, even more preferably of five bacteria listed in Table 2 in the biopsy is a diagnostic marker of papulopustular rosacea (PPR).

A further object of the invention relates to a method of controlling and measuring an active agent's treatment effectiveness on rosacea in a patient in need thereof, the method comprising characterizing specific microbiota associated with *Demodex* mites from the patient before and after treating the patient.

It is a further object of the invention to provide a kit for diagnosing rosacea comprising means for analyzing and characterizing a microbiota associated with *Demodex* mites in a biological sample.

DETAILED DESCRIPTION OF THE INVENTION

Definitions

Figure 1:
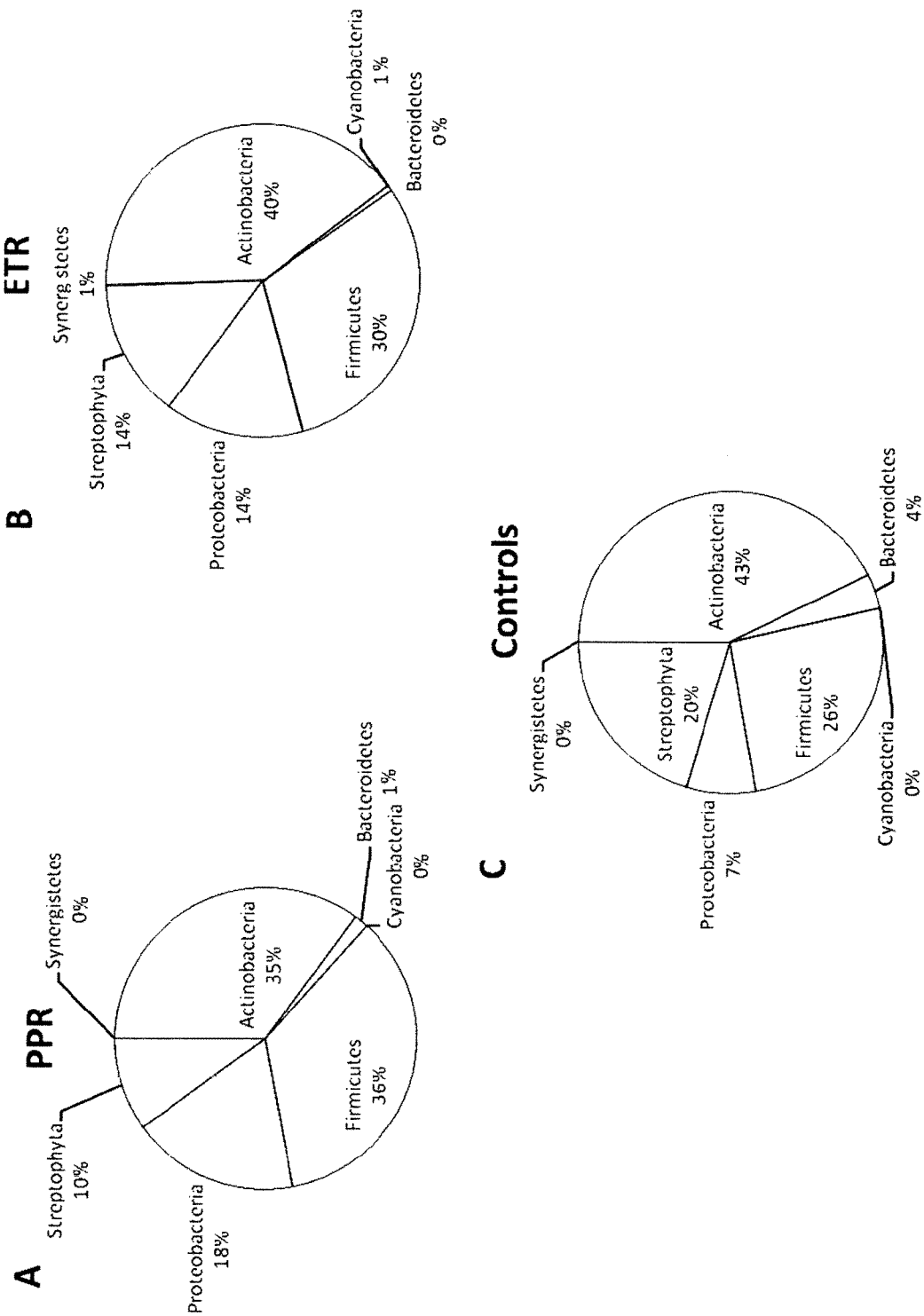
FIG. 1: Proportion of sequences found per phylum in PPR group (A), ETR group (B) and Controls (C) in Example 1.

The present disclosure will be best understood by reference to the following definitions.

*Demodex* is a genus of tiny parasitic mites that live in or near hair follicles of mammals. The Demodicidae family contains 140 species of *Demodex* mites, which are known to colonize the skin of eleven orders of mammals, including humans. More particularly, two species have been identified as living in human: *Demodex folliculorum*, which is found in hair follicles and *Demodex brevis* which lives in sebaceous glands connected to hair follicles. These parasites are found asymptomatically in the hair follicle, the follicular infundibulum and the sebaceous and Meibomian glands, mostly on the face near the nose, the eyelashes and eyebrows, but also occur elsewhere on the body. In elderly people, the prevalence could reach 100%.

In the context of the invention, the term "biopsy" refers to any cell or tissue sample removed from a subject, which may contain *Demodex* mites. For example, the biopsy used in the context of the invention is a skin sample or a skin hair follicle samples. In the present application, "biological sample", "sample" and "biopsy" are used indifferently to refer to such a sample.

In the context of the invention, "prevalence" describes a proportion, for example expressed as a percentage. For instance, the prevalence of Gram negative bacteria refers to the proportion of Gram negative bacteria among the microbiota population considered.

In the context of the invention, "reference sample", "control sample" or "control" are used indifferently to refer to a biological sample taken from a healthy subject, i.e. with no active skin disease. In the context of assessment of treatment efficiency, samples from the same subject at different times may also be used, for instance to follow up of a therapeutic approach at different stages of the treatment, for instance before the beginning of the treatment and at different stages of the treatment. The control may also be taken from a subject who is responder or non-responder to a tested treatment. Advantageously, the control sample is of the same type and from the same area as the biological sample to test, e.g. when the test sample is skin, the control sample is a skin sample from the same area.

For the purpose of the present invention, the term "marker" or "indicator" denotes a biological marker associated with the presence or with the absence of a specific pathological state. More particularly, a marker or indicator of rosacea refers to a biological data allowing to diagnosis or to the contrary rule out with certainty rosacea, or subtype thereof, in a subject. In the present case, the inventors have discovered that data relative to the microbiota of *Demodex* mites may be used to determine whether a subject presents rosacea or not and/or to discriminate between two specific subtypes of rosacea in a subject exhibiting rosacea.

In the context of the invention, "the presence of X in a biopsy" or "the prevalence of X in a biopsy" is intended to refer more specifically to the presence or prevalence of X in the microbiota of *Demodex* mites contained in the biopsy.

Methods of DNA Sequencing

The inventors have surprisingly discovered that the microbiota associated with *Demodex* mites presents some differences in healthy subjects and rosacea subjects that may be useful for in vitro diagnostic of the disease.

In order to characterize and analyze the microbiota associated with *Demodex* mites, molecular techniques such as the construction of library based on cloning of the 16SrRNA gene or pyrosequencing may be used.

For instance, a method of 16SrRNA sequencing is implemented using oligonucleotides specifically hybridizing with 16S ribosomal genes for gene amplification, through PCR. Otherwise, pairs of universal primers, such as 8F and 1510R (Weisburg et al (January 1991). "16S ribosomal DNA amplification for phylogenetic study". J Bacteriol. 173 (2): 697-703.), may be used. Further, the oligonucleotides used as primers may be obtained by chemical synthesis.

It is therefore an object of the invention to characterize the bacterial repertoire of *Demodex* mites via a 16SrRNA clone library. Advantageously, the analysis is performed using DNA extracted from a single mite to establish the variability of the bacterial content of individual mites.

Comparative analysis of the microbiota of *Demodex* mites collected from several subjects are then possible, and the data relative to the microbiota of *Demodex* may be further used in a method of diagnosing rosacea.

In the same way, a method of pyrosequencing of 16SrRNA may be used, based on the Illumina sequencing by synthesis technology, using the MiSeq benchtop instrument. First, 16SrRNA PCR are performed on individual mites which are then pooled per group for subsequent sequencing analysis. Said technology is well known by the person skilled in the art (see for instance Singh et al, Mol Biol Rep, 2012, 39(12): 10595-602).

The *Demodex*-Specific Microbiota is a Diagnostic Marker of Rosacea

By performing characterization of the *Demodex*-specific microbiota of rosacea patients, the inventors have discovered that the prevalence of Gram negative bacteria in the *Demodex*-specific microbiota is increased in a rosacea subject compared to healthy subject. More particularly, the inventors have discovered that specific species of bacteria are over-represented or conversely under-represented in the *Demodex*-specific microbiota of rosacea patients, and that the study of this microbiota may allow to confirm or infirm a rosacea diagnosis in a patient.

It is therefore an object of the invention to provide a method for the diagnosis of rosacea in a patient comprising a step of characterizing a microbiota associated with *Demodex* in a biological sample.

According to an embodiment, the method comprises a preliminary step of providing a biopsy, or biological sample, of the patient, which would be used for the characterization step.

In a specific embodiment, the biological sample is a skin sample. For instance, the skin sample may be taken by means of tape stripping, such as with D-Squames, according to the method described in Wong R et al., "Analysis of RNA recovery and gene expression in the epidermis using non-invasive tape stripping"; J Dermatol Sci. 2006 November; 44(2):81-92; or in Benson N R, et al., "An analysis of select pathogenic messages in lesional and non-lesional psoriatic skin using non-invasive tape harvesting". J Invest Dermatol. 2006 October; 126(10): 2234-41; or else in Wong R et al., "Use of RT-PCR and DNA microarrays to characterize RNA recovered by non-invasive tape harvesting of normal and inflamed skin". J Invest Dermatol. 2004 July; 123 (1): 159-67. According to the principle of tape stripping, the product used comprises a flexible translucent polymer support and an adhesive. The product is applied repeatedly to the skin of the patient, preferably until loss of adhesion. The sample obtained relates only to the content of the outermost layers of the epidermis.

In another specific embodiment, the sample may be a hair follicle sampled according to the method described in Patent Application WO2009/053493 (Galderma R&D). This method describes in particular the non-invasive sampling of a hair follicle and also a method for analysing the latter in order to identify the expression profile of the genes or markers.

According to an embodiment of the present invention, the prevalence of Gram negative bacteria in the microbiota associated with *Demodex* is used as a diagnostic marker of rosacea. More particularly, an increase of the prevalence of Gram negative bacteria in a biological sample, compared to a healthy control, is a diagnostic marker of rosacea.

In the context of the invention, an increase of the prevalence of bacteria means that the amount of bacteria is at least 1.2 fold higher in the sample compared to a healthy control, preferably at least 1.4 fold higher and more preferably at least 1.8 fold higher. In the same way, a decrease of the prevalence of bacteria means that the amount of bacteria is at least 1.2 fold lower in the sample compared to a healthy control, preferably at least 1.4 fold lower and more preferably at least 1.8 fold lower.

Among the *Demodex microbiota*, some species are more specifically associated with the rosacea condition, which belong to Firmicutes, Actinobacteria, Proteobacteria, Bacteroidetes, Cyanobacteria and Synergistetes.

Therefore, according to an embodiment of the method of the invention, an increase of the prevalence of at least one bacterium selected from the group of Firmicutes, Actinobacteria, Proteobacteria, Bacteroidetes, Synergistetes and Cyanobacteria, preferably from the group of Firmicutes, Actinobacteria and Proteobacteria, even more preferably from the group of Firmicutes and Proteobacteria, is a diagnostic marker of rosacea.

In a specific embodiment, an increase of the prevalence of Proteobacteria, preferably of *Bartonella* and/or *Escherichia*, is a diagnostic marker of papulopustular rosacea or erythematotelangiectatic rosacea.

In a specific embodiment, an increase of *Bartonella* in the biological sample, compared to a healthy control, is a diagnostic marker of erythematotelangiectatic rosacea.

In a specific embodiment, a decrease of the prevalence of Actinobacteria in the biological sample, compared to a healthy control, is a diagnostic marker of papulopustular rosacea (PPR).

Furthermore, the inventors have discovered that some species of bacteria are specifically associated with specific subtypes of rosacea. More particularly, specific species of bacteria, mainly belonging to Firmicutes and Proteobacteria, are associated with erythematotelangiectatic rosacea or papulopustular rosacea, respectively.

Examples of bacteria species found specifically in ETR patients and PPR patients are summarized below.

TABLE 1

Species specifically associated with ETR

| Species | Phylum |
| --- | --- |
| Acinetobacter schindleri | Proteobacteria |
| Amaricoccus kaplicensis | Proteobacteria |
| Anabaena augstumalis | Cyanobacteria |
| Bartonella quintana | Proteobacteria |
| Duganella zoogloeoides | Proteobacteria |
| Methylobacterium extorquens | Proteobacteria |
| Methylobacterium tardum | Proteobacteria |
| Neisseria flavescens | Proteobacteria |
| Neisseria perflava | Proteobacteria |
| Niastella populi | Bacteroidetes |
| Ochrobactrum tritici | Proteobacteria |
| Propionispora hippei | Firmicutes |
| Pseudomonas boreopolis | Proteobacteria |
| Pyramidobacter piscolens | Synergistetes |
| Rhodobacter johrii | Proteobacteria |
| Sphingomonas yanoikuyae | Proteobacteria |
| Sporolituus thermophilus | Firmicutes |
| Stenotrophomonas rhizophila | Proteobacteria |
| Aciditerrimonas ferrireducens | Actinobacteria |
| Aerococcus viridans | Firmicutes |
| Anaerococcus prevotii | Firmicutes |
| Bacillus frigoritolerans | Firmicutes |
| Bacillus macroides | Firmicutes |
| Brevibacterium album | Actinobacteria |
| Brevibacterium antiquum | Actinobacteria |
| Brevibacterium oceani | Actinobacteria |
| Clostridium aminovalericum | Firmicutes |
| Clostridium sordellii | Firmicutes |
| Corynebacterium mucifaciens | Actinobacteria |
| Exiguobacterium aestuarii | Firmicutes |
| Gemella sanguinis | Firmicutes |

TABLE 1-continued

Species specifically associated with ETR

| Species | Phylum |
| --- | --- |
| Geobacillus debilis | Firmicutes |
| Geobacillus tepidamans | Firmicutes |
| Jeotgalicoccus psychrophilus | Firmicutes |
| Lactobacillus iners | Firmicutes |
| Micrococcus luteus | Actinobacteria |
| Paenibacillus barengoltzii | Firmicutes |
| Paenibacillus macerans | Firmicutes |
| Peptostreptococcus stomatis | Firmicutes |
| Planomicrobium glaciei | Firmicutes |
| Streptococcus cristatus | Firmicutes |
| Streptococcus thermophilus | Firmicutes |
| Veillonella dispar | Firmicutes |
| Veillonella montpellierensis | Firmicutes |
| Thermoanaerobacterium calidifontis | Firmicutes |
| Thermoanaerobacterium aotearoense | Firmicutes |

TABLE 2

Species specifically associated with PPR

| Species | Phylum |
| --- | --- |
| Acinetobacter calcoaceticus | Proteobacteria |
| Acinetobacter pittii | Proteobacteria |
| Aquabacterium fontiphilum | Proteobacteria |
| Comamonas kerstersii | Proteobacteria |
| Curvibacter delicatus | Proteobacteria |
| Escherichia coli | Proteobacteria |
| Ferrovum myxofaciens | Proteobacteria |
| Massilia alkalitolerans | Proteobacteria |
| Methylobacterium gregans | Proteobacteria |
| Methylobacterium thiocyanatum | Proteobacteria |
| Pantoea agglomerans | Proteobacteria |
| Paracoccus homiensis | Proteobacteria |
| Pelomonas puraquae | Proteobacteria |
| Photobacterium damselae | Proteobacteria |
| Pleomorphomonas oryzae | Proteobacteria |
| Reyranella massiliensis | Proteobacteria |
| Rhizobium giardinii | Proteobacteria |
| Sphingomonas paucimobilis | Proteobacteria |
| Tepidimonas arfidensis | Proteobacteria |
| Clostridium celatum | Firmicutes |
| Friedmanniella spumicola | Actinobacteria |
| Geobacillus jurassicus | Firmicutes |
| Leuconostoc mesenteroides | Firmicutes |
| Nocardiopsis composta | Actinobacteria |
| Nocardiopsis synnemataformans | Actinobacteria |
| Paenisporosarcina quisquiliarum | Firmicutes |
| Planomicrobium okeanokoites | Firmicutes |
| Ruminococcus bromii | Firmicutes |
| Staphylococcus haemolyticus | Firmicutes |
| Streptococcus suis | Firmicutes |
| Trichococcus pasteurii | Firmicutes |
| Turicibacter sanguinis | Firmicutes |

TABLE 3

Species shared with PPR patients and ETR patients and absent in healthy subjects

| Species | Phylum |
| --- | --- |
| Acidovorax caeni | Proteobacteria |
| Enterobacter cloacae | Proteobacteria |
| Hydrogenophilus thermoluteolus | Proteobacteria |
| Ochrobactrum grignonense | Proteobacteria |
| Petrobacter succinatimandens | Proteobacteria |
| Stenotrophomonas maltophilia | Proteobacteria |
| Zoogloea resiniphila | Proteobacteria |
| Nocardiopsis dassonvillei | Actinobacteria |

The table 4 below summarizes Gram Negative bacteria found in rosacea patients and the number of *Demodex* in which they have been found.

TABLE 4

Gram Negative bacteria found in ETR and PPR groups

| Species | ETR | PPR |
|---|---|---|
| *Acidovorax caeni* | x | x |
| *Acinetobacter calcoaceticus* |  | x |
| *Acinetobacter pittii* |  | x |
| *Acinetobacter schindleri* | x |  |
| *Amaricoccus kaplicensis* | x |  |
| *Anabaena augstumalis* | x |  |
| *Aquabacterium fontiphilum* |  | x |
| *Bartonella quintana* | x |  |
| *Comamonas kersterii* |  | x |
| *Curvibacter delicatus* |  | x |
| *Duganella zoogloeoides* | x |  |
| *Enterobacter cloacae* | x | x |
| *Escherichia coli* |  | x |
| *Ferrovum myxofaciens* |  | x |
| *Hydrogenophilus thermoluteolus* | x | x |
| *Massilia alkalitolerans* |  | x |
| *Methylobacterium extorquens* | x |  |
| *Methylobacterium gregans* |  | x |
| *Methylobacterium tardum* | x |  |
| *Methylobacterium thiocyanatum* |  | x |
| *Neisseria flavescens* | X |  |
| *Neisseria perflava* | X |  |
| *Niastella populi* | X |  |
| *Ochrobactrum grignonense* | X | x |
| *Ochrobactrum tritici* | x |  |
| *Pantoea agglomerans* |  | x |
| *Paracoccus homiensis* |  | x |
| *Pelomonas puraquae* |  | x |
| *Petrobacter succinatimandens* | x | x |
| *Photobacterium damselae* |  | x |
| *Pleomorphomonas oryzae* |  | x |
| *Propionispora hippei* | x |  |
| *Pseudomonas boreopolis* | x |  |
| *Pyramidobacter piscolens* | x |  |
| *Reyranella massiliensis* |  | X |
| *Rhizobium giardinii* |  | x |
| *Rhodobacter johrii* | x |  |
| *Sphingomonas paucimobilis* |  | x |
| *Sphingomonas yanoikuyae* | x |  |
| *Sporolituus thermophilus* | x |  |
| *Stenotrophomonas maltophilia* | x | x |
| *Stenotrophomonas rhizophila* | x |  |
| *Tepidimonas arfidensis* |  | x |
| *Zoogloea resiniphila* | x | x |

Furthermore, the invention discloses a method of differentiating a subtype of rosacea in a patient with rosacea, comprising a step of characterizing a microbiota associated with *Demodex* mites in a biological sample taken from a patient with rosacea, wherein the prevalence of Gram negative bacteria in the microbiota associated with *Demodex* mites is used as a diagnostic marker of erythematotelangiectatic rosacea or papulopulstular rosacea.

The invention further discloses a method of differentiating a subtype of rosacea comprising the step of comparing the prevalence of Proteobacteria and/or Actinobacteria in a biological sample taken from a patient with rosacea with a healthy control, an increase of Proteobacteria and/or a decrease of Actinobacteria, compared to the control, being a diagnostic marker of papulopustular rosacea.

It is a further object of the invention to provide a method for monitoring the efficacy of a treatment intended for treating rosacea, comprising the step of characterizing a microbiota associated with *Demodex* mites in a biological sample taken from a patient with rosacea before and after treating the patient. Accordingly, a sample is provided before and after the treatment of said patient.

In a particular embodiment, the method for monitoring the efficacy of the treatment further comprises the step of analyzing the prevalence of Gram negative bacteria in said microbiota, before and after treating the patient.

For instance, a decrease of the prevalence of Gram negative bacteria could be associated to an efficient treatment for treating rosacea.

Preferentially, all these methods are performed using a skin sample or a skin hair follicle sample.

It is a further object of the invention to provide a kit for diagnosing rosacea comprising means for analyzing and characterizing the *Demodex*-specific microbiota in a biological sample, such as skin sample.

For example, the kit comprises specific primers and/or probes hybridizing with 16S ribosomal genes.

The invention also relates to the use of a kit comprising means for analyzing and characterizing the *Demodex*-specific microbiota in a biological sample for diagnosing or subtyping rosacea.

The following Examples and Figures illustrate the invention without limiting its scope.

EXAMPLES

The implied role of *Demodex* mites in rosacea remains controversial. An increase in the density of these mites in patients seems to be associated with the papulopustular form of rosacea but not erythematotelangiectatic rosacea. However, a small number of studies failed to demonstrate an increase in *Demodex* density in patients with rosacea. To our knowledge, only one bacterial strain, *Bacillus oleronius*, has been isolated from these mites by culturing. Moreover, culture-dependent studies do not allow for a consistent picture of the skin microbiota to be obtained. A more reliable approach would be the use of molecular techniques, such as the construction of a library based on the cloning of the 16SrRNA gene or pyrosequencing. We focused on the characterization of the bacterial repertoire of *Demodex* mites via a 16S rRNA clone library. Furthermore, we analyzed the microbiota of *Demodex* separately with a reproducible protocol based on the extraction of DNA from a single mite to establish the variability of the bacterial content of individual mites. These studies report the results of comparative analysis of the microbiota of *Demodex* mites collected from rosacea patients (ETR and PPR) and controls.

Example 1

Material and Methods
Sampling
*Demodex* Folliculorum sampling was performed using standardized skin surface biopsy (SSSB). This is a non-invasive sampling method by which it is possible to collect the superficial part of the horny layer and the complete follicle contents. With this technique it is possible to analyse the composition of microorganisms present in each layer.

Two successive samplings were performed on the naso-labial fold of patients with erythematotelangiectatic rosacea (ETR), papulopustular rosacea (PPR) and Healthy volunteers using a modified protocol of the formerly described method. The *Demodex* Folliculorum were separated under microscope from other parasites and debris before genomic analysis. Approximately fifteen samples per group were obtained and sent to us by ProDerm (Germany, Hamburg). Samples were conserved at −80° C. after reception.

Observation and Separation of *Demodex*

After centrifugation at 4722 g for 10 minutes, the bottom of the Eppendorf tube was cut with a scalpel and oil was collected on a Petri dish. *Demodex* were then observed under ×115 magnification with the Olympus SZX16. *Demodex* mites were separated and collected in sterile Eppendorf tube containing paraffin oil using a micro forceps (Electron Microscopy Sciences, France, Ayguesvives). Samples were stored at −80° C. prior to further analysis.

External Decontamination

As for external decontamination of *Demodex* mites, 500 µl PBS were added to the oil and centrifuged at 295 g for 1 minute in order to separate the oily phase from the aqueous phase containing the mite. The oil was removed and these steps were repeated twice before the complete removal of the PBS; 500 µl of 70% ethanol were then added and the sample centrifuged under the same conditions. Another wash was performed with ethanol followed by two washes with PBS. As for sterility control, 100 µl of the supernatant obtained after the last centrifugation step of the decontamination protocol described above were poured on Columbia 5% sheep blood agar (Biomerieux, France, Marcy l'Etoile) at 37° C. overnight. Decontamination was repeated as long as the culture was not negative.

DNA Extraction

For DNA extraction, grinding was performed with a sterile micro pilon (Tebu-bio, France, Le Perray en Yvelines) after the immersion in liquid nitrogen for one minute. Half of the sample was conserved at −80° C. The 200 µl left were used for DNA extraction. First, a mechanical lysis step was required using glass micro beads. Samples were inserted in a FastPrep-24 apparatus (MP Biomedicals Europe, France, Illkirch-Graffenstaden) and submitted to two series of one minute at 6.5 m·s−1 shaking. A centrifugation step at 16162 g for one minute was necessary for the precipitation of beads. Then, the samples were divided in two and subjected to an overnight lysis at 56° C. with 100 µl of tissue lysis buffer and 20 µl of proteinase K from the QIAmp DNA Mini Kit (Qiagen, France, Courtaboeuf). On the next day, samples were further incubated at 70° C. for 10 minutes with 200 µl of lysis buffer. After the addition of 200 µl of absolute ethanol, solutions were transferred to QiAmp Mini Spin Columns and the protocol was performed as described by the supplier. Finally, DNA was eluted in 50 µl of supplier's buffer and directly analyzed by real time PCR (see below).

Bacterial 16SrDNA Gene Library Construction

A *Demodex* canis ITS gene (GenBank GU299785.1) specific real-time PCR (rt PCR) was designed using Primer3 v0.4.0 software comprising of a probe DemoITS 6FAM-TGGGTTGATTGACAAACGCTTTTGAG (SEQ ID No 1) (Applied Biosystems, France, Courtaboeuf), a forward DemoITSF and reverse DemoITSR primers with respective sequences 5'-CAAAAGCCCGTAAGAAGCAC-3' (SEQ ID No 2) and 5'-ATTGGCCTTCGCCTTTACTT-3' (SEQ ID No 3) (Eurogentec, Belgium, Seraing).

A second rt PCR system targeting the 16SrRNA gene was used in parallel in order to rapidly screen the samples to submit to cloning. It comprised a probe VIC-CGTCRTC-CCCRCCTTCC (SEQ ID No 4) (Applied Biosystems), a forward primer 1391R 5'-GACGGGCGGTGTGTRCA-3' (SEQ ID No 5) and a reverse primer 1099F 5'-GYAAC-GAGCGCAACCC-3' (SEQ ID No 6) (Eurogentec). Each test was realized using 5 picomoles of primers and probes with 5 µl of extracted DNA unless for the negative control which was done in quadruplates. A synthetic primer containing the ITS gene amplicon of 357 bp obtained by using the primers described above was used a positive control for the *demodex* extraction. For the system targeting the 16S rRNA gene, the positive control consisted of a bacterial suspension. Rt PCR reactions were performed on MXM3000™ apparatus (Stratagene Europe, Netherlands, Amsterdam) using the mix QuantiTect (Qiagen) with the following program: 95° C. for 15 minutes followed by 45 cycles alternating a step at 95° C. for 30 seconds and a second one of 1 minute at 60° C. As for 16SrRNA PCR, two pairs of universal primers consisting of the forward primer 8F 5'-AGAGTTTGATCCTGGCTCAG-3' (SEQ ID No 7) with either the reverse primer 1510R 5'-CGGTTACCTTGT-TACGACTT-3' (SEQ ID No 8) or 1391R 5'-GACGGGCG-GTGTGTRCA-3' (SEQ ID No 9) (Eurogentec) were used to amplify the 16S rRNA gene as previously reported.

Reactions were performed in a final volume of 50 µl with 5 µl DNA, 5 picomoles of primers, 200 mM of each dNTP and 0.5 U of Taq. Amplification was done following a program with a cycle at 94° C. for 15 minutes, 45 cycles with a denaturation step at 94° C. for 30 seconds, hybridization for 45 seconds at 52° C. when using 1510R and 55° C. for 1391R and an elongation at 72° C. for 2 minutes, final elongation was made at 72° C. for 5 minutes.

As for 16S rRNA cloning, amplicons were purified and ligated on pGEM-T Easy Systems vectors (Promega, France, Charbonnieres) at a molar ratio of 3:1. Then, ligation's products were transformed into thermo competent cells JM109 (Promega) and cultured overnight on selective agar dishes containing 0.5 mM IPTG, 40 µg/ml XGal and 100 µg/ml ampicillin. White colonies were screened for the insert by PCR using forward primer M13F 5'-CGCCA-GGGTTTTCCCAGTCACGAC-3' (SEQ ID No 10) and M13R 5'-TCACACAGGAAACAGCTATGA-3' (SEQ ID No 11) (Eurogentec) with the following program: 94° C. for 15 minutes, 40 cycles alternating denaturation at 94° C. for 30 seconds, hybridization at 57° C. for 45 seconds and elongation at 72° C. for 3 minutes, final elongation at 72° C. for 5 minutes. Efficiently transformed clones were revealed on agarose gel by a band corresponding to a fragment of 1500 bp.

Sequence Analysis

Sequencing reaction were performed using eight primers chosen to cover the whole amplicon sequence and the BigDye Terminator 1.1 Cycle Sequencing kit (Applied Biosystem) on an ABI Prism 3100 apparatus (Applied Biosystem). Sequences obtained were manually corrected and aligned using the ChromasPro software. Contigs were confronted to the BLASTn nucleotide collection database and identification was considered reliable to the species-level when identity was above 98.7%.

Biodiversity, Phylogenetic Analysis and Statistical Comparison Between Libraries Using MOTHUR, sequences were aligned with elimination of those that did not start at the position were 90% of sequences did and that contained ambiguous nucleotides. Then, sequences were clustered as OTUS at an overlap identity cutoff of 98%. Richness was estimated using nonparametric estimators Chao1 and abundance-based coverage estimator (ACE) and diversity was assessed calculating the Shannon diversity index. The diversity of OTUs and community overlap were examined using rarefaction analysis and Venn diagram.

Difference between clone libraries was estimated using weighted unifrac approach.

Statistical Analysis

Statistical analyses were performed using R software.

Comparison of means and proportions were assessed using the Kruskal-Willis H test and the Fisher Exact test respectively.

Results

Collection of *Demodex*

Out of the fifteen samples obtained from healthy volunteers, nine contained no *Demodex* mites compared to three and four for the ETR and PPR groups respectively. There were significantly less samples containing *Demodex* mites in the control group when compared to rosacea groups (p=0.023). By the end, it means that we obtained 29 samples with *Demodex* that is 5 for controls, 12 for ETR, and 11 for PPR.

From these twenty nine samples, 335 *Demodex* mites were isolated that is 15 from controls, 94 for ETR, and 227 for PPR. According to the Kruskal-Wilis H test, there were statistically less *Demodex* per sample in controls than in ETR and PPR groups with a p value of 0.01579.

DNA Extraction and Detection of 16SrRNA Gene

Thanks to the real time PCR targeting the ITS gene, we were able to confirm our extraction protocol with a global efficiency of 85.37% that is 72, 148 and 11 positive samples for the respective ETR, PPR and control groups.

By using the real time PCR system specific for the 16SrRNA gene, extracts were screened for the presence of bacterial DNA. Noteworthy detection of bacterial DNA was observed in 83% of mites that is 11, 72 and 148 for the controls, ETR and PPR groups respectively.

16S rRNA Clone Library

Only 103 out of the 231 positive by real time PCR were confirmed by classic PCR that is 8, 36 and 59 for controls, ETR and PPR groups respectively. The cloning efficiency rate was of 69.99% with only 72 sets of amplicons being cloned i.e. 37 out of 59 for PPR, 27 out of 36 for ETR and 8 out of 8 for controls.

A total of 428 sequences were obtained that is 174, 200 and 54 with a mean number of sequences per *Demodex* of 6.44, 5.40 and 6.75 in ETR, PPR and controls groups respectively.

Description of the Global Bacterial Repertoire

According to the BLASTn results, a total of 122 different species were identified that is 85 with homology above 98.7% and 37 corresponding to new species (Tables 5A and 5B below). New species represented 41.17%, 29.23% and 21.87% of all species and 14.81%, 13.79% and 9.5% of sequences in the control, the ETR and PPR groups respectively. No statistical difference was achieved.

The number of species found per *Demodex* ranges from one to eight in the control group with a mean value of 3.25 and a median of 3. In mites from rosacea patients it ranges from one to ten and eleven with respective mean values of 4.03 and 3.57 and median values of 4 and 2 for ETR and PPR groups.

Interestingly, the most represented phylum (i.e. the phylum with the greater percentage of sequences) was Firmicutes in PPR group whereas it was Actinobacteria in ETR group and controls (FIG. 1). Nevertheless, there was no statistical difference in the proportion of sequences belonging to Actinobacteria and Firmicutes between the three groups (respective p values of 0.104 and p=0.39). The proportion of sequences related to Proteobacteria was statistically higher in the PPR group (23%) compared to ETR (14.36%) and controls (7.4%), p=0.01.

Figure 2:
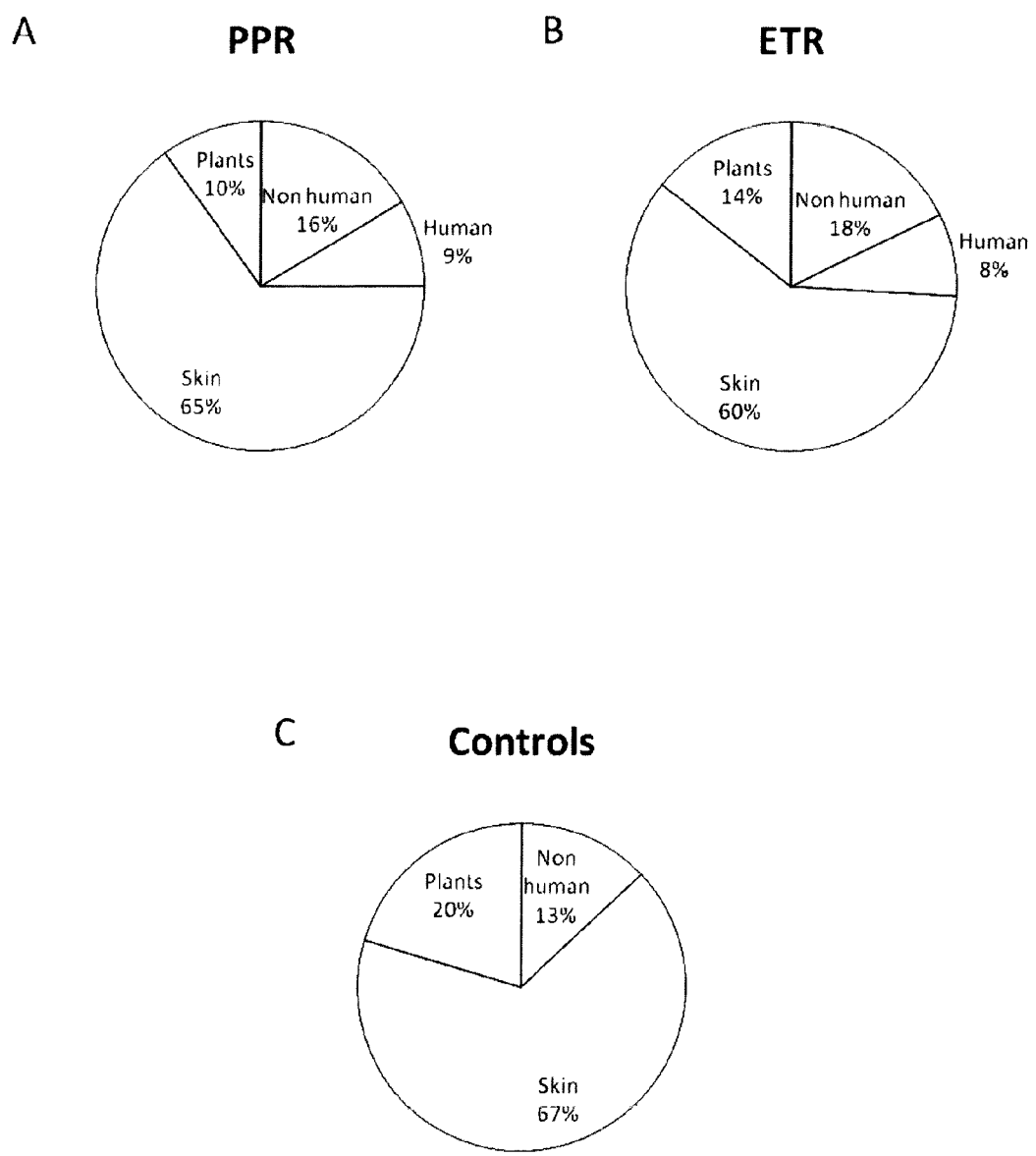
FIG. 2: Proportion of sequences per ecosystem in PPR group (A), ETR group (B) and Controls (C) in Example 1. Plant sequences (phylum: Streptophyta) corresponded to 10-24% of sequences in the three groups. More than 60% of all sequences corresponded to species that had already been described in culture-independent studies of human skin microbiota. Between 13 to 18% of sequences corresponded to species that had never been reported on humans.

It is noteworthy that plant sequences (phylum: Streptophyta) corresponded to 10-24% of sequences in the three groups. More than 60% of all sequences corresponded to species that had already been described in culture-independent studies of human skin microbiota. Between 13 to 18% of sequences corresponded to species that had never been reported on humans (FIG. 2).

Tables 5A and 5B: Tables listing identified species of bacteria with number of *Demodex* associated in Experimentation 1.

TABLE 5A

Specific bacterial pattern found in ETR patients

| Species | Nb demodex |
|---|---|
| *Aerococcus viridans* | 1 |
| *Anaerococcus prevotii* | 1 |
| *Anoxybacillus amylolyticus* | 1 |
| *Bacillus macroides* | 1 |
| *Bartonella quintana* | 3 |
| *Brevibacterium album* | 2 |
| *Brevibacterium oceani* | 1 |
| *Corynebacterium mucifaciens* | 1 |
| *Corynebacterium pseudogenitalium* | 1 |
| *Duganella zoogloeoides* | 6 |
| *Exiguobacterium aestuarii* | 1 |
| *Gemella haemolysans* | 1 |
| *Haemophilus parainfluenzae* | 1 |
| *Jeotgalicoccus psychrophilus* | 3 |
| *Lactobacillus iners* | 1 |
| *Methylobacterium longum* | 1 |
| *Micrococcus luteus* | 1 |
| *Moraxella osloensis* | 1 |
| *Neisseria flavescens* | 1 |
| *Sphingomonas yanoikuyae* | 2 |
| *Staphylococcus warneri* | 1 |
| *Stenotrophomonas rhizophila* | 1 |
| *Streptococcus australis* | 1 |
| *Streptococcus sanguinis* | 4 |
| *Streptococcus thermophilus* | 2 |
| *Streptococcus tigurinus* | 1 |
| *Tetracoccuscechii* | 1 |
| *Veillonella montpellierensis* | 1 |
| *Aciditerrimonas ferrireducens* | 1 |
| *Actinomyces viscosus* | 1 |
| *Anabaena augstumalis* | 1 |
| *Anoxybacillus amylolyticus* | 1 |
| *Brevibacterium antiquum* | 1 |
| *Brevibacterium frigotolerans* | 2 |
| *Brevibacterium linens* | 1 |
| *Clostridium sordellii* | 2 |
| *Gemella sanguinis* | 1 |
| *Mesorhizobium loti* | 1 |
| *Neisseria lactamica* | 2 |
| *Neisseria perflava* | 1 |
| *Niastella populi* | 2 |
| *Pyramidobacter piscolens* | 1 |
| *Veillonella dispar* | 1 |

TABLE 5B

Specific bacterial pattern found in PPR patients

| Species | Nb demodex |
|---|---|
| *Acinetobacter calcoaceticus* | 3 |
| *Acinetobacter pittii* | 7 |
| *Aquabacterium fontiphilum* | 4 |
| *Bacillus thermoamylovorans* | 1 |
| *Clostridium disporicum* | 1 |
| *Comamonas kerstersii* | 1 |
| *Comamonas testosteroni* | 1 |
| *Curvibacter delicatus* | 1 |
| *Escherichia coli* | 2 |
| *Friedmanniella spumicola* | 1 |
| *Granulicatella para-adiacens* | 2 |
| *Lactobacillus sakei* | 6 |
| *Leuconostoc mesenteroides* | 1 |

TABLE 5B-continued

Specific bacterial pattern found in PPR patients

| Species | Nb demodex |
|---|---|
| *Massilia alkalitolerans* | 2 |
| *Massilia timonae* | 1 |
| *Paenisporosarcina quisquiliarum* | 2 |
| *Pantoea agglomerans* | 1 |
| *Pantoea brenneri* | 1 |
| *Petrobacter succinatimandens* | 1 |
| *Pseudomonas oleovorans* | 2 |
| *Pseudomonas saccharophila* | 1 |
| *Sphingomonas paucimobilis* | 1 |
| *Staphylococcus equorum* | 1 |
| *Staphylococcus haemolyticus* | 2 |
| *Stenotrophomonas maltophilia* | 3 |
| *Streptococcus mitis/pneumoniae* | 6 |
| *Streptococcus salivarius* | 1 |
| *Tepidimonas arfidensis* | 1 |
| *Trichococcus pasteurii* | 1 |
| *Turicibacter sanguinis* | 1 |
| *Undibacterium oligocarboniphilum* | 1 |
| *Ferrovum myxofaciens* | 1 |
| *Naxibacter haematophilus* | 1 |
| *Neisseria meningitidis* | 1 |
| *Paracoccus homiensis* | 1 |
| *Pedobacter daechungensis* | 1 |
| *Propionibacterium acnes* | 3 |
| *Propionivibrio limicola* | 1 |
| *Reyranella massiliensis* | 1 |
| *Staphylococcus epidermidis* | 2 |
| *Staphylococcus haemolyticus* | 1 |
| *Streptococcus suis* | 1 |

Description of the Shared Repertoire

Only four known bacterial species were common to the three groups: *Propionibacterium acnes, Staphylococcus epidermidis, Streptococcus mitis*, and *Corynebacterium kroppenstedtii*. *Castanea mollissima* sequences (Streptophyta) were obtained from the three groups. The proportions of these five species in term of sequences were statistically different as they accounted for 51.72%, 46% and 68.52% of all sequences in the ETR, PPR and control groups respectively (p=0.013) but not in term of *Demodex* containing these sequences that is 85.18%, 75.7% and 75% of *Demodex* from the ETR, PPR and control groups respectively (p=0.64). One unknown species with best hit BLAST corresponding to *Neisseria animaloris* was also present in the three groups.

Description of the Group-Specific Bacterial Repertoire

Most of the species identified were found to be group-specific (i.e. found in only one group). Forty-four species were only found in ETR group, representing 46.7% of sequences with 18 species corresponding to unknown species. Six species were only found in controls that is 12.96% of sequences. Among them five were unknown species. Forty-two species representing 43% of sequences were specific to PPR group with twelve corresponding to unknown species (Tables 5A-5B).

By analyzing the microbiota specific to the ETR and PPR groups, we noticed that three species known to be human pathogens have been identified in these mites: *Bartonella quintana, Escherichia coli* and *Haemophilus parainfluenzae*. None of these species were found in control group. In term of sequence proportions these three species corresponded to 0.6% and 4% of all sequences obtained from the ETR and PPR groups respectively. 29 species out of the 85 identified at a species-level were Gram-negative bacteria i.e. 35.29%. They were found in statistically more *Demodex* from ETR group than in PPR and controls (results not shown).

The Table 6 below shows the list of Gram-negative bacteria specifically present in ETR and PPR groups, but not found in healthy patients.

TABLE 6

List of identified species of Gram-negative in ETR and PPR groups with number of Demodex

| Gram-negatives pecies | ETR | HV | PPR |
|---|---|---|---|
| *Actinomyces viscosus* | 1 | — | — |
| *Anabaena augstumalis* | 1 | — | — |
| *Brevibacterium antiquum* | 1 | — | — |
| *Brevibacterium frigotolerans* | 2 | — | — |
| *Brevibacterium linens* | 1 | — | — |
| *Clostridium sordellii* | 2 | — | — |
| *Ferrovum myxofaciens* | — | — | 1 |
| *Gemella sanguinis* | 1 | — | — |
| *Jatropha curcas* | 1 | — | — |
| *Mesorhizobium loti* | 1 | — | — |
| *Naxibacter haematophilus* | — | — | 1 |
| *Neisseria lactamica* | 2 | — | — |
| *Neisseria meningitidis* | — | — | 1 |
| *Neisseria perflava* | 1 | — | — |
| *Niastella populi* | 2 | — | — |
| *Paracoccus homiensis* | — | — | 1 |
| *Pedobacter daechungensis* | — | — | 1 |
| *Propionivibrio limicola* | — | — | 1 |
| *Pyramidobacter piscolens* | 1 | — | — |
| *Reyranella massiliensis* | — | — | 1 |
| *Streptococcus suis* | — | — | 1 |
| *Veillonella dispar* | 1 | — | — |

Comparison of the Three Communities

Using MOTHUR, a total of 120 OTUs were identified using the average neighbor algorithm at a cutoff value of 0.02. It has to be reminded that prior to OTU assignment, a pre-treatment had been made removing 40 sequences that started after the 1044rd nucleotide position in order to obtain a final alignment of 684 nucleotides (12.21 and 6 for the ETR, PPR and control groups respectively).

A venn diagram showed that the total richness was of 120 OTUs with only 5 shared between the three groups. Six OTUs were shared between *Demodex* from ETR and PPR groups as against 4 between PPR and controls and only one between ETR and controls. Total group richness was of 58, 65 and 18 for the ETR, PPR and control groups. Rarefaction curves showed that the sampling effort was equivalent between the three groups and as they did not reach a plateau, more species might be found when increasing it (results not shown).

Shannon diversity index was slightly increased in ETR and PPR groups as compared to controls with respective values of 3.38, 3.40 and 2.25 at a 0.01 OTU definition level. The highest richness diversity estimator values were obtained for PPR group with respective ACE and Chao1 values of 234.17 and 133.33 at a 0.01 OTU definition level as against respective values of 110.46 and 101.15 for ETR and 76.13 and 29 for controls. Weighted unifrac algorithm was applied to the tree generated thanks to the distance matrix obtained. Pairwise comparison showed that the three communities were statistically different, p<0.001.

The three communities had statistically different structures with increased diversity and richness in *Demodex* from rosacea patients.

Example 2

Materials and Methods

Study Population 55 subjects from the general population of Schenefeld/Hamburg and the neighboring communities so that 45 subjects were enclosed: 15 subjects with erythematotelangiectatic rosacea with flushing and persistent central facial erythema, optional telangiectasia (mean age 54.89±10.49), 15 subjects with papulopustular rosacea defined as moderate to severe with persistent central facial erythema, transient papules and/or pustules (mean age 50.86±11.2) from the Galderma rosacea database and 15 healthy subjects with no active skin disease (mean age 52.38±13.68). Subjects with rosacea received no treatment and were asked to stop treatment with Benzylbenzoate, Lindan, Pyrethrin, Malathion, Allethrin, Crotamiton and Metronidazole at least 7 days before sampling.

Sampling

Standardized skin surface biopsies were performed on the alar crease (side of the nostrils) of patients with erythematotelangiectatic rosacea (ETR) and papulopustular rosacea (PPR), along with control patients, according to a modified protocol of a formerly described method consisting of two consecutive samplings on the same area. The second standardized skin surface biopsy was used for observation and transfer of *Demodex* mites to Eppendorf tubes containing paraffin oil. Fifteen tubes per group were obtained and sent to us by ProDerm (Hamburg, Germany). Samples were preserved at −80° C. after receipt.

Observation and Separation of *Demodex*
See example 1.
External Decontamination
See example 1.
DNA Extraction
See example 1.
Bacterial 16S rDNA Gene Library Construction
See example 1.
Sequence Analysis
See example 1.
Biodiversity, Phylogenetic Analysis and Statistical Comparison Between Libraries Sequences were aligned using MOTHUR. Sequences were eliminated whenever they did not start at the starting position shared by 90% of sequences or contained ambiguous nucleotides, or both. Then, sequences were clustered as OTUs with an overlap identity cutoff of 99% using the nearest neighbor algorithm. Each OTU taxonomic label was identified as the consensus taxonomic label. Here, consensus was shared by more than 50% of the sequences comprised in the OTU when challenged against nucleotide BLAST database. Whenever identity to the consensus label was below 98.7%, the OTU was considered as a new phylotype. Representative clones for each OTU corresponded to the longest sequence in the OTU.

Observed richness was compared between the three groups using rarefaction curves.

A Venn diagram was used to represent the repartition of OTUs among the three groups.

Alpha diversity (diversity within communities) was assessed using species-based measures such as the Simpson's inverse index and the non parametric Shannon Weiner index which was further used for community evenness calculation. Community richness was estimated using the nonparametric abundance-based coverage estimator (ACE).

Distance matrix based on previous alignment was calculated with the R software using the seqinr. Then, phylogenetic tree was constructed based on a neighbor-joining algorithm with the ape library. This tree was further used to assess community beta diversity using the divergence-based measure unweighted UniFrac on the website. http://bmf.colorado.edu/unifrac/. Significance tests were calculated using Monte Carlo simulations.

Statistical Analysis

See example 1.

Results

Increased Density and Prevalence of *Demodex* Mites in Rosacea Patients

Prevalence was increased in rosacea patients as compared to controls. From the 45 samples collected, 28 contained *Demodex*: 12, 11 and 5 for the ETR, PPR and control groups, respectively. There were significantly fewer samples containing *Demodex* mites in the control group compared to the rosacea groups (33.33% vs 80% and 73.33%, p=0.023). Furthermore, density was increased in rosacea patients as compared to controls. From these twenty-eight samples, 335 *Demodex* mites were separated: 93 from ETR, 227 from PPR and 15 from controls. Mean density of *Demodex* was 6.88-fold increased in PPR as compared to controls (20.64 vs 3) and 2.66-fold in PPR as compared to ETR patients (20.64 vs 7.75). According to the Kruskal-Wallis H test, there were significantly fewer *Demodex* per sample in controls than for the ETR and PPR groups, with a p value of 0.01579.

DNA Extraction and 16SrRNA Clone Library Construction

Even though presence of *Demodex* mites was confirmed through observation under magnification during the protocol establishment after either collection or washing steps, the hypothesis of losing mites during these steps could not be ruled out. Only DNA extracts found positive by ITS real-time PCR were, thus, considered for further analysis. A total of 286 *Demodex* mites were included in this study; that is 86, 187 and 13 for the ETR, PPR and control groups, respectively.

In parallel to ITS real-time PCR, extracts were screened for the presence of bacterial DNA using a real-time PCR system that was specific for the 16S rRNA gene. Noteworthy detection of bacterial DNA was observed in 231 extracts (80.77% of mites) that is, 72, 148 and 11 for the ETR, PPR and control groups respectively.

From the 231 extracts that were positive by real-time PCR, only 103 were also found to be positive by classical PCR; we identified 36, 59 and 8 positive extracts for the ETR, PPR and control groups, respectively. The cloning efficiency rate was 69.90%, with only 72 sets of amplicons being cloned, specifically 27 out of 36 for ETR, 37 out of 59 for PPR and 8 out of 8 for the controls.

A total of 428 clones were obtained; that is, 174, 200 and 54 clones. The mean number of clones per *Demodex* was the same between the three groups with a mean number of 6.44, 5.41 and 6.75 clones per extract for the ETR, PPR and control groups, respectively.

Microbiota of *Demodex* Mites

The Table 7 below summarizes the OTUs found in *Demodex* mites.

TABLE 7

List of 121 OTUs identified in Demodex mites

| OTU | Consensus taxonomic label | Clones number (ETR; PPR; controls) | Phylum | Ecosystem |
|---|---|---|---|---|
| 1 | *Lactobacillus sakei* | 4 (0;0;4) | *Firmicutes* | Skin |
| 2 | *Staphylococcus epidermidis* | 56 (19;8;29) | *Firmicutes* | Skin |
| 3 | *Propionibacterium acnes* | 87 (29;18;40) | *Actinobacteria* | Skin |
| 4 | *Streptococcus mitis* | 9 (2;7;0) | *Firmicutes* | Skin |
| 5 | *Geobacillus tepidamans* | 2 (2;0;0) | *Firmicutes* | Non human |
| 6 | *Veillonella montpellierensis* | 2 (2;0;0) | *Firmicutes* | Human |
| 7 | *Exiguobacterium aestuarii* | 1 (1;0;0) | *Firmicutes* | Non human |
| 8 | *Gemella haemolysans* | 1 (1;0;0) | *Firmicutes* | Skin |
| 9 | *Jeotgalicoccus psychrophilus* | 3 (3;0;0) | *Firmicutes* | Skin |
| 10 | *Aerococcus viridans* | 1 (1;0;0) | *Firmicutes* | Skin |
| 11 | *Streptococcus sanguinis* | 2 (2;0;0) | *Firmicutes* | Skin |
| 12 | *Bartonella quintana* | 3 (3;0;0) | *Proteobacteria* | Human |
| 14 | *Paenisporosarcina quisquiliarum* | 2 (0;2;0) | *Firmicutes* | Non human |
| 15 | *Aquabacterium fontiphilum* | 1 (0;1;0) | *Proteobacteria* | Non human |
| 16 | *Pseudomonas oleovorans* | 2 (0;2;0) | *Proteobacteria* | Non human |
| 17 | *Corynebacterium kroppenstedtii* | 2 (0;2;0) | *Actinobacteria* | Skin |
| 18 | *Lactobacillus sakei* | 1 (0;1;0) | *Firmicutes* | Skin |
| 19 | *Comamonas testosteroni* | 1 (0;1;0) | *Proteobacteria* | Human |
| 20 | *Undibacterium oligocarboniphilum* | 1 (0;1;0) | *Proteobacteria* | Skin |
| 21 | *Acinetobacter pittii* | 7 (0;7;0) | *Proteobacteria* | Human |
| 24 | *Streptococcus mitis* | 5 (3;2;0) | *Firmicutes* | Skin |
| 25 | *Finegoldia magna* | 3 (1;0;2) | *Firmicutes* | Skin |
| 27 | *Ochrobactrum grignonense* | 2 (1;1;0) | *Proteobacteria* | Non human |
| 29 | *Acinetobacter calcoaceticus* | 3 (0;3;0) | *Proteobacteria* | Skin |
| 30 | *Leuconostoc mesenteroides* | 1 (0;1;0) | *Firmicutes* | Skin |
| 31 | *Corynebacterium kroppenstedtii* | 1 (0;1;0) | *Proteobacteria* | Skin |
| 32 | *Streptococcus mitis* | 2 (0;2;0) | *Firmicutes* | Skin |
| 33 | *Granulicatella para-adiacens* | 1 (0;1;0) | *Firmicutes* | Human |
| 34 | *Staphylococcus epidermidis/hominis* | 1 (0;1;0) | *Firmicutes* | Non human |
| 35 | *Mucilaginibacter rigui* | 1 (0;0;1) | *Bacteroidetes* | Non human |
| 36 | *Streptococcus mitis* | 3 (2;0;1) | *Firmicutes* | Skin |
| 37 | *Corynebacterium kroppenstedtii* | 20 (17;1;2) | *Actinobacteria* | Skin |
| 42 | *Curvibacter gracilis* | 2 (0;1;1) | *Proteobacteria* | Non human |
| 43 | *Curvibacter gracilis* | 2 (0;2;0) | *Proteobacteria* | Non human |
| 44 | *Trichococcus pasteurii* | 1 (0;1;0) | *Firmicutes* | Non human |
| 45 | *Stenotrophomonas maltophilia* | 2 (0;2;0) | *Proteobacteria* | Skin |
| 46 | *Sphingomonas paucimobilis* | 1 (0;1;0) | *Proteobacteria* | Skin |
| 48 | *Streptococcus mitis/oralis* | 2 (2;0;0) | *Firmicutes* | Non human |
| 50 | *Streptococcus salivarius* | 1 (0;1;0) | *Firmicutes* | Skin |
| 53 | *Streptococcus parasanguinis* | 1 (0;1;0) | *Firmicutes* | Skin |
| 54 | *Granulicatella para-adiacens* | 1 (0;1;0) | *Firmicutes* | Human |
| 56 | *Acinetobacter pittii* | 1 (0;1;0) | *Proteobacteria* | Human |
| 57 | *Brevibacterium album* | 2 (2;0;0) | *Actinobacteria* | Non human |
| 58 | *Duganella zoogloeoides* | 5 (5;0;0) | *Proteobacteria* | Non human |
| 59 | *Duganella zoogloeoides* | 1 (1;0;0) | *Proteobacteria* | Non human |
| 60 | *Staphylococcus haemoiyticus/hominis* | 2 (0;2;0) | *Firmicutes* | Non human |
| 61 | *Escherichia coli* | 1 (0;1;0) | *Proteobacteria* | Skin |
| 62 | *Stenotrophomonas rhizophila* | 1 (1;0;0) | *Proteobacteria* | Non human |
| 64 | *Escherichia coli* | 1 (0;1;0) | *Proteobacteria* | Skin |
| 65 | *Stenotrophomonas maltophilia* | 1 (0;1;0) | *Proteobacteria* | Skin |
| 66 | *Propionibacterium granulosum* | 1 (0;1;0) | *Actinobacteria* | Skin |
| 69 | *Staphylococcus equorum* | 1 (0;1;0) | *Firmicutes* | Non human |
| 74 | *Streptococcus mitis/pneumoniae* | 2 (1;1;0) | *Firmicutes* | Non human |
| 75 | *Bacillus thermoamylovorans* | 1 (0;1;0) | *Firmicutes* | Non human |
| 78 | *Comamonas kerstersii* | 1 (0;1;0) | *Proteobacteria* | Non human |
| 80 | *Turicibacter sanguinis* | 1 (0;1;0) | *Firmicutes* | Human |
| 85 | *Staphylococcus warneri* | 1 (1;0;0) | *Firmicutes* | Skin |
| 86 | *Methylobacterium tardum* | 1 (1;0;0) | *Proteobacteria* | Non human |
| 88 | *Haemophilus parainfluenzae* | 1 (1;0;0) | *Proteobacteria* | Skin |
| 89 | *Brevibacterium oceani* | 2 (2;0;0) | *Actinobacteria* | Non human |

TABLE 7-continued

List of 121 OTUs identified in Demodex mites

| OTU | Consensus taxonomic label | Clones number (ETR; PPR; controls) | Phylum | Ecosystem |
|---|---|---|---|---|
| 91 | Corynebacterium tuberculostearicum | 1 (0;1;0) | Actinobacteria | Skin |
| 92 | Micrococcus luteus | 1 (0;1;0) | Actinobacteria | Skin |
| 94 | Streptococcus thermophilus | 1 (0;1;0) | Firmicutes | Non human |
| 95 | Neisseria flavescens | 1 (0;1;0) | Proteobacteria | Skin |
| 98 | Streptococcus thermophilus | 1 (0;1;0) | Firmicutes | Non human |
| 99 | Propionibacterium granulosum | 2 (2;0;0) | Actinobacteria | Skin |
| 102 | Lactobacillus iners | 1 (0;1;0) | Firmicutes | Human |
| 103 | Moraxella osloensis | 1 (0;1;0) | Proteobacteria | Human |
| 104 | Streptococcus oralis | 2 (2;0;0) | Firmicutes | Human |
| 111 | Aquabacterium fontiphilum | 1 (0;1;0) | Proteobacteria | Non human |
| 112 | Streptococcus pneumoniae | 1 (0;1;0) | Firmicutes | Skin |
| 116 | Streptococcus mitis | 1 (0;1;0) | Firmicutes | Skin |
| 120 | Lactobacillus sakei | 1 (0;1;0) | Firmicutes | Skin |
| 121 | Staphylococcus epidermidis | 2 (0;2;0) | Firmicutes | Skin |

According to results from the Nucleotide Basic Local Alignment Search Tool (BLASTn), 55 sequences corresponded to Streptophyta sp. (plant pollens) and were thus omitted. Furthermore, 31 sequences were excluded because they started after the first nucleotide. By the end, 342 sequences were analyzed that is 140 for ETR, 162 for PPR and 40 for controls. These sequences were grouped into 121 Operational Taxonomic Units (OTUs) sharing 99% similarity with 84 singletons (including only one clone) and only 3 grouping more than 10 clones. Only 23 of the 121 OTUs identified in this study were found in more than one mites (19%).

Among these 121 OTUs, 53 corresponded to Firmicutes, 45 corresponded to Proteobacteria, 18 corresponded to Actinobacteria, 3 to Bacteroidetes, 1 to Cyanobacteria and 1 to Synergistetes (Table 7). The most represented phylum (i.e., the phylum gathering the greater percentage of clones) was Firmicutes with 140 clones (that is 40.94%). Even though more OTUs belonged to Proteobacteria than to Actinobacteria, more clones belonged to Actinobacteria than to Proteobacteria with respectively 127 and 67 clones. Among total OTUs, 47 were new phylotypes that is sharing a percentage of identity with the consensus taxonomic label inferior to 98.7% with 42 singletons. All OTUs were grouped according to their former description either as part of human skin microbiota (referred as "skin species"), or another human microbiota (referred as "human species") or none (referred as "non-human species"). New phylotypes were considered as "non human". 72 OTUs were associated with "non-human species" (60.33%), followed by "skin species" (37 OTUs) and "human species" (12 OTUs). Still, the most represented group was "skin species" who gathered 226 clones (66.08%) as against only 94 clones for "non human species" (27.49%) and 22 clones for "human species" (6.43%). "Non human species" could be considered as Demodex-specific microbiota. Only 8.33% of these species were shared by more than one Demodex (6 OTUs). "Non human species" corresponded to Proteobacteria (44 clones, 46.81%) followed by Firmicutes (30 clones, 31.91%), Actinobacteria (12 clones, 12.77%), Bacteroidetes (6 clones, 6%), Synergistetes (1 clone, 1.06%) and Cyanobacteria (1 clone, 1.06%). "Non human species" were highly associated to Gram-negative species ($p<10^{-6}$).

Overall, Demodex microbiota shows a predominance of Firmicutes followed by Actinobacteria, Proteobacteria, Bacteroidetes, Cyanobacteria and Synergistetes with most of the clones corresponding to known members of human skin microbiota.

Comparison of the Three Communities

Figure 3:
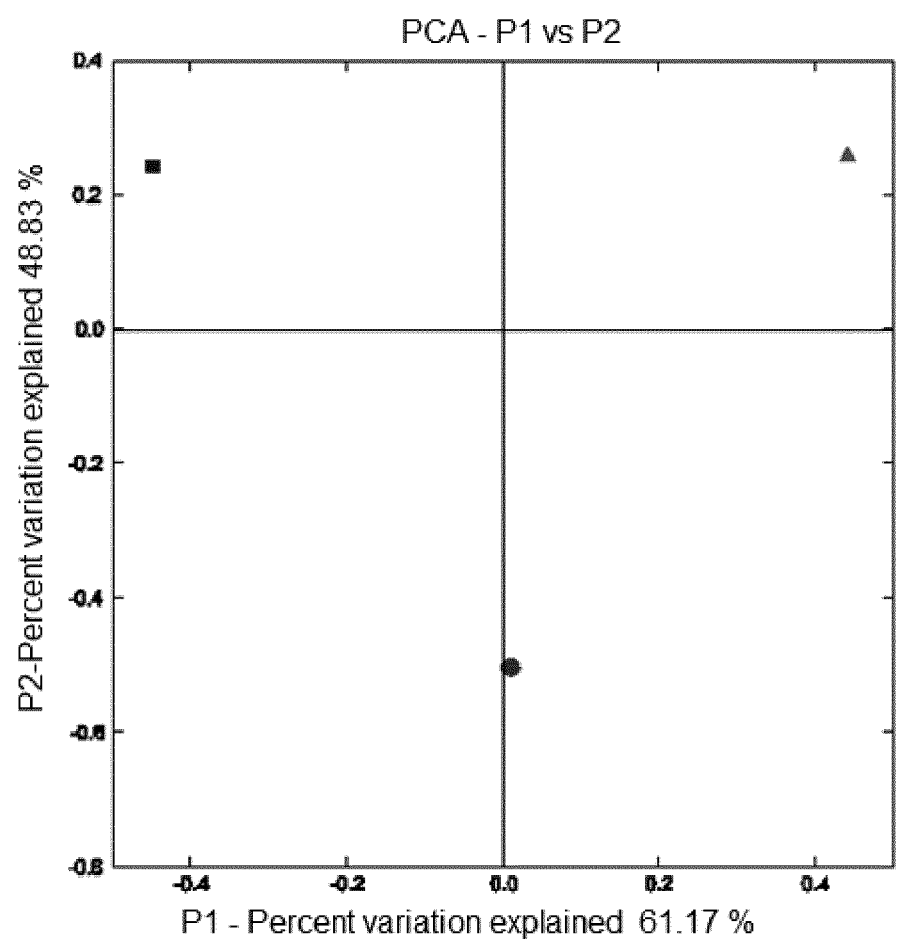
FIG. 3: Pairwise comparison by UniFrac analysis of *Demodex* from ETR, PPR and controls of Example 2. Principal component analysis with clusterization of ETR patients (square), PPR patients (triangle) and controls (circle).

Increased Diversity in Demodex from Rosacea Patients: Increased Evenness in ETR and Increased Richness in PPR Pairwise comparison revealed that the three communities were significantly different by an unweighted unifrac analysis ($p \leq 0.003$) with distances between ETR and controls of 0.8758, between ETR and PPR of 0.8909 and between PPR and controls of 0.8751 and as shown with PC A (FIG. 3).

Figure 4:
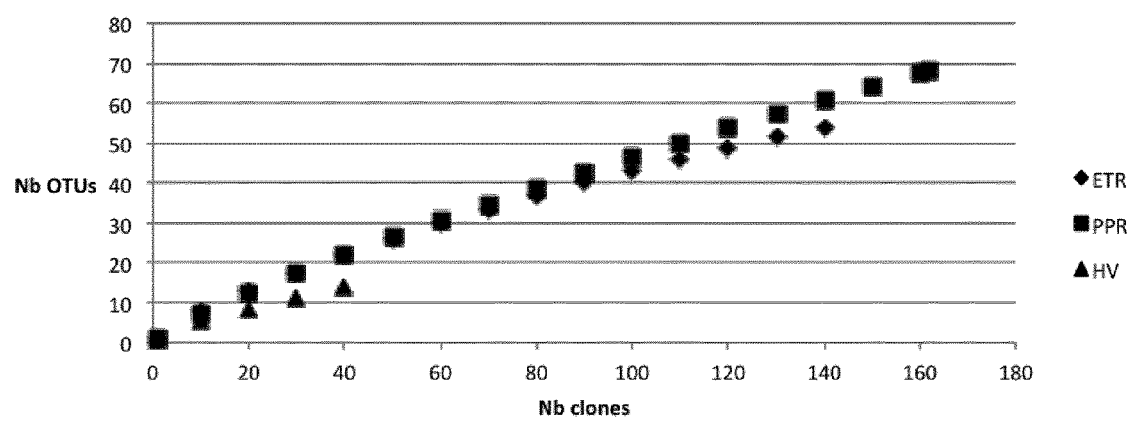
FIG. 4: Graphic depicting the relationship between the number of OTUs and the number of clones of Example 2 shows that the microbial diversity is underestimated. Rarefaction curves show the number of species identified according to the sampling effort in ETR patients (diamond shape), PPR patients (square) and controls (triangle).

Overall richness was different between the three communities with ACE values of 105.19, 587.62 and 154.7 for ETR, PPR and control groups respectively (as shown by the Kruskal Wallis test with $p=0.00067$). Surprisingly, richness was increased in control group as compared to ETR group. Comparison with the observed richness (54, 68 and 14 for the ETR, PPR and control groups respectively) highlights the underestimation of the real diversity which is confirmed by the slope of rarefaction curves (FIG. 4).

PPR-associated microbiota was the richest with ACE values significantly increased as compared to ETR and control groups (respective p values 0.001067 and 0.008129). Diversity was highly different between communities with Inverse Simpson's indices of 13.03, 10.23 and 4.26 for ETR, PPR and control groups ($p \leq 10^{-5}$). ETR-associated microbiota was the most diverse. This increased diversity was associated with an increased evenness as compared to PPR ($p=0.022$). Control group was the least even community with one OTU accounting for roughly 45% of all clones.

The three communities had significantly different structures with increased diversity in Demodex from rosacea patients, increased evenness in ETR and increased richness in PPR.

PPR-Associated Microbiota of Demodex Mites Differed from ETR and Controls with Decreased Proportion of Actinobacteria and Increased Proportion of Proteobacteria.

Figure 5:
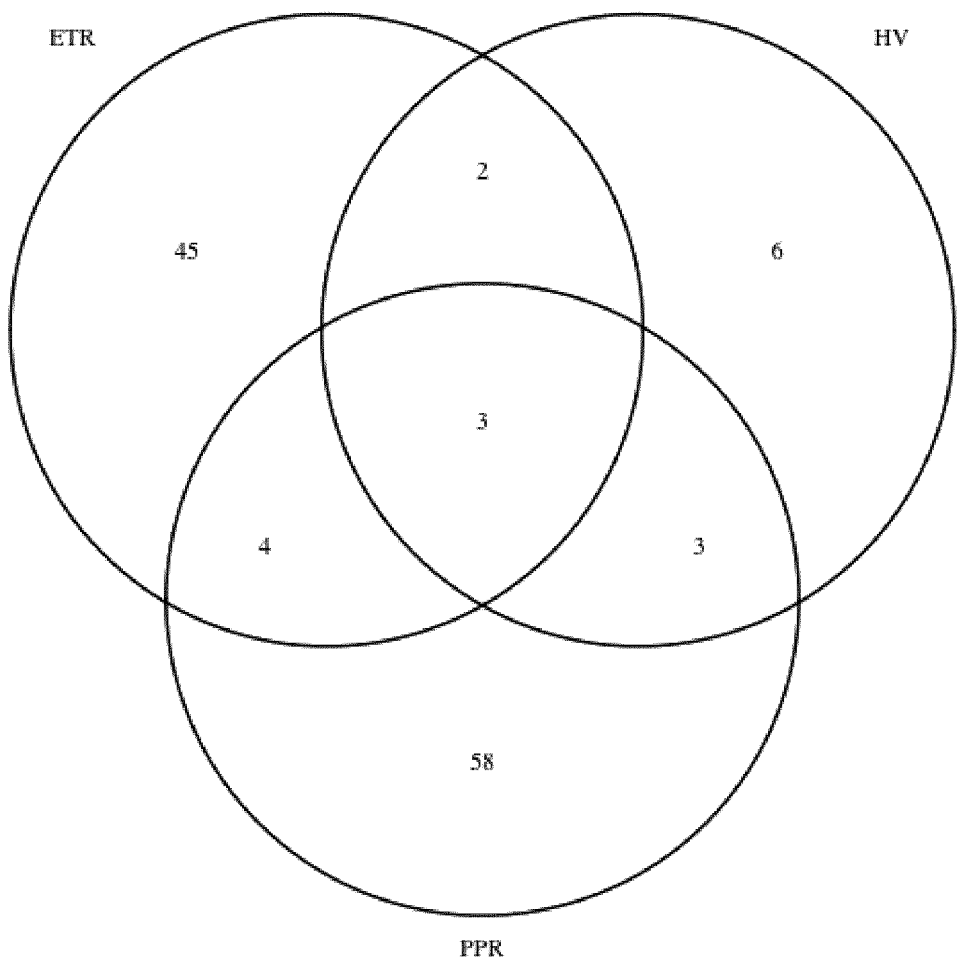
FIG. 5: Venn diagram showing the repartition of OTUs in Example 2 according to the groups

The number of OTUs per group varied with 54 in the ETR group, 68 for the PPR group and 14 for the control group. The core microbiota consisted of three OTUs that were common to the three groups (core microbiota) with consensus taxonomic labels were Corynebacterium kroppenstedtii (OTU 2), Propionibacterium acnes (OTU 3) and Staphylococcus epidermidis (OTU 37) as shown in the Venn diagram (FIG. 5).

Altogether, these three OTUs comprised 163 clones (i.e. 65, 70 and 28 clones for the ETR, PPR and control groups). The proportion of clones belonging to OTU2 was significantly increased in the ETR group as compared to the PPR group (17/140 vs 1/162, p=2.14 $10^{-5}$). OTU 3 represented 29, 40 and 18 clones for respective groups ETR, PPR and controls; showing an increased prevalence in the control group as compared to the ETR and PPR groups (18/40 vs 29/140, p=0.0038 and 18/40 vs 40/162, p=0.018 respectively). *Demodex*-associated microbiota is highly dependent on the origin group with 37.73% of clones belonging to the core microbiota that is 2.48% of all identified OTUs.

Interestingly, the most represented phylum was Firmicutes in the PPR group, whereas Actinobacteria was the most highly represented in both the ETR and control groups. Besides, on the one hand, the proportion of Actinobacteria was significantly decreased in the PPR group as shown by the Fisher test between ETR and PPR (58/140 vs 48/114, p=0.03974) as well as between PPR and controls (48/114 vs 21/40, p=0.00886). On the other hand, the proportion of Proteobacteria was significantly increased in the PPR group as compared to the controls (42/162 vs 4/40, p=0.03507). Among Proteobacteria, species belonging to the class Gamma-Proteobacteria were significantly increased in PPR as compared to ETR (19/42 vs 3/24, p=0.0073).

Figure 6:
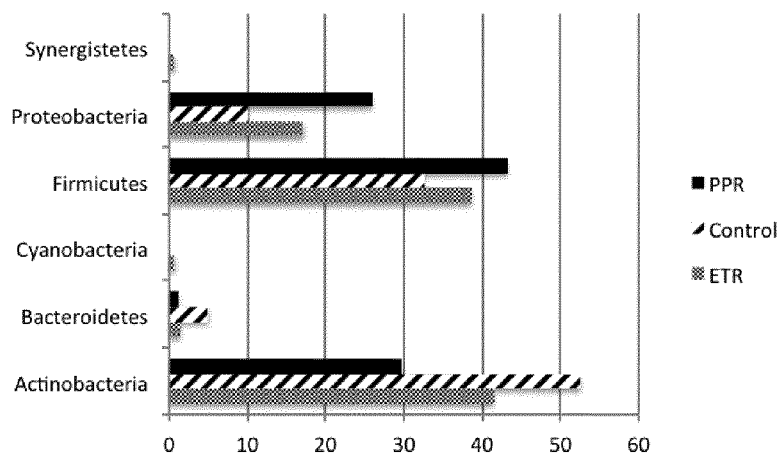
FIG. 6: Graphic showing the repartition of phyla in the ETR (dotted bar), PPR (filled bar) and control (striped bar) as a percentage of sequences according to Example 2. The Results show an increased proportion of Proteobacteria along with decreased proportion of Actinobacteria in PPR patients.

In ETR, 41% of clones were Actinobacteria, 40% were Firmicutes, 16% were Proteobacteria and Bacteroidetes, Cyanobacteria and Synergistetes represented 1% of clones each (FIG. 6). In PPR, 44% of clones were Firmicutes, 30% were Actinobacteria, 25% were Proteobacteria and 1% was Bacteroidetes (FIG. 6). In controls, 52% were Actinobacteria, 33% were Firmicutes, 10% were Proteobacteria and 5% were Bacteroidetes (FIG. 6).

In the three groups, Actinobacteria and Firmicutes were predominated by "skin species" whereas Proteobacteria were majoritarily "non human species".

Besides, genera known to be human pathogens were only identified in rosacea groups: *Bartonella* and *Haemophilus* in the ETR group and *Escherichia* in the PPR group.

The Table 8 below summarizes the repartition of phyla of Gram negative bacteria in ETR patients, PPR patients and controls (HV).

TABLE 8 repartition of phyla of Gram negative bacteria in ETR, PPR and HV

| % Group | Actinobacteria | Bacteroidetes | Cyanobacteria | Firmicutes | Proteobacteria | Synergistetes | Total |
|---|---|---|---|---|---|---|---|
| ETR | 41.63624651 | 0.901868155 | 1.481640541 | 37.04101353 | 18.48829719 | 0.450934078 | 100 |
| HV | 59.87654321 | 3.703703704 | 0 | 26.54320988 | 9.87654321 | 0 | 100 |
| PPR | 29.94571162 | 0.496292995 | 0 | 48.90815541 | 20.64983997 | 0 | 100 |

Example 3

Materials and Methods

Study Population 81 subjects from the general population of Schenefeld/Hamburg and the neighboring communities so that 60 subjects were enclosed: 15 subjects with erythematotelangiectatic rosacea with flushing and persistent central facial erythema, optional telangiectasia (mean age 52.8±10.86), 15 subjects with papulopustular rosacea defined as moderate to severe with persistent central facial erythema, transient papules and/or pustules (mean age 51.46±9.14) from the Galderma rosacea database and 30 healthy subjects with no active skin disease (mean age 51.9±13.31). Subjects with rosacea received no treatment and were asked to stop treatment with Benzylbenzoate, Lindan, Pyrethrin, Malathion, Allethrin, Crotamiton and Metronidazole at least 7 days before sampling.

Sampling
See example 2
Observation and Separation of *Demodex*
See example 1.
External Decontamination
See example 1.
DNA Extraction
See example 1.
Bacterial 16S rDNA Gene Library Construction
See example 1.
Sequence Analysis
See example 1.
Statistical Analysis
See example 1.
Results
Microbiota of *Demodex* Mites The Table 9 below shows the list of Gram-negative bacteria specifically present in ETR and PPR groups, but not found in healthy patients, and the number of *Demodex* in which they have been found.

TABLE 9

Gram Negative bacteria found in ETR and PPR groups

| Strains | ETR | PPR |
|---|---|---|
| *Acidovorax caeni* | 1 | 1 |
| *Acinetobacter calcoaceticus* |  | 3 |
| *Acinetobacter pittii* |  | 7 |
| *Acinetobacter schindleri* | 1 |  |
| *Aggregatibacter aphrophilus* |  | 1 |
| *Amaricoccus kaplicensis* | 1 |  |
| *Anabaena augstumalis* | 1 |  |
| *Aquabacterium fontiphilum* |  | 4 |
| *Bartonella quintana* | 3 |  |
| *Comamonas kersterii* |  | 1 |
| *Curvibacter delicatus* |  | 1 |
| *Duganella zoogloeoides* | 6 |  |
| *Enterobacter cloacae* | 1 | 1 |
| *Escherichia coli* |  | 2 |
| *Ferrovum myxofaciens* |  | 1 |

TABLE 9-continued

Gram Negative bacteria found in ETR and PPR groups

| Strains | ETR | PPR |
|---|---|---|
| *Massilia alkalitolerans* |  | 2 |
| *Methylobacterium extorquens* | 1 |  |
| *Methylobacterium gregans* |  | 1 |
| *Methylobacterium tardum* | 1 |  |
| *Methylobacterium thiocyanatum* |  | 1 |
| *Neisseria flavescens* | 1 |  |
| *Neisseria perflava* | 1 |  |
| *Neisseria weaveri* |  | 1 |
| *Niastella populi* | 2 |  |
| *Ochrobactrum grignonense* | 1 | 1 |

TABLE 9-continued

Gram Negative bacteria found in ETR and PPR groups

| Strains | ETR | PPR |
| --- | --- | --- |
| Ochrobactrum tritici | 4 | |
| Pantoea agglomerans | | 1 |
| Paracoccus homiensis | | 1 |
| Pelomonas puraquae | | 1 |
| Petrobacter succinatimandens | 2 | 5 |
| Photobacterium damselae | | 1 |
| Pleomorphomonas oryzae | | 2 |
| Propionispora hippei | 2 | |
| Pseudomonas boreopolis | 1 | |
| Pyramidobacter piscolens | 1 | |
| Reyranella massiliensis | | 1 |
| Rhizobium giardinii | | 1 |
| Rhodobacter johrii | 1 | |
| Sphingomonas paucimobilis | | 1 |
| Sphingomonas yanoikuyae | 1 | |
| Sporolituus thermophilus | 1 | |
| Stenotrophomonas maltophilia | 1 | 1 |
| Stenotrophomonas rhizophila | 1 | |
| Tepidimonas arfidensis | | 1 |
| Veillonella dispar | 1 | |
| Veillonella montpellierensis | 2 | |
| Zoogloea resiniphila | 1 | 1 |

According to these results, 6 Gram negative bacteria are common to PPR and ETR, while 21 Gram negative bacteria are associated solely to ETR, and 19 to PPR.

The invention claimed is:

1. A method of characterizing specific microbiota associated with *Demodex* mites obtained from a patient suspected of rosacea, the method comprising:
   (a) isolating *Demodex* mites from a biological sample of the patient;
   (b) isolating DNA from the *Demodex* mites; and
   (c) analyzing the microbiota in the biopsy based on a method of 16SrRNA sequencing or pyrosequencing.

2. A method of detecting bacteria associated with rosacea subtype Erythematotelangiectatic Rosacea (herein "ETR") or Papulopustular Rosacea (herein "PPR") in a patient suspected of rosacea, the method comprising:
   (a) isolating *Demodex* mites from a biological sample of the patient;
   (b) isolating DNA from the *Demodex* mites;
   (c) using 16S rRNA gene sequencing or pyrosequencing techniques to determine the nucleic acid sequences of bacterial DNA isolated from *Demodex* mites; and
   (d) analyzing the nucleic acid sequence of step (c) to detect one or more ETR bacteria or PPR bacteria, wherein the bacteria is selected from the group consisting of *Aciditerrimonas ferrireducens; Acidovorax caeni; Acinetobacter calcoaceticus; Acinetobacter pittii; Acinetobacter schindleri; Actinomyces viscosus; Aerococcus viridans; Amaricoccus kaplicensis; Anabaena augstumalis; Anaerococcus prevotii; Anoxybacillus amylolyticus; Aquabacterium fontiphilum; Bacillus frigoritolerans; Bacillus macroides; Bartonella quintana; Brevibacterium album; Brevibacterium antiquum; Brevibacterium frigotolerans; Brevibacterium linens; Brevibacterium oceani; Clostridium aminovalericum; Clostridium celatum; Clostridium sordellii; Comamonas kersterii; Corynebacterium mucifaciens; Corynebacterium pseudo genitalium; Curvibacter delicatus; Duganella zoogloeoides; Enterobacter cloacae; Escherichia coli; Exiguobacterium aestuarii; Ferrovum myxofaciens; Friedmanniella spumicola; Gemella haemolysans; Gemella sanguinis; Geobacillus debilis; Geobacillus jurassicus; Geobacillus tepidamans; Haemophilus parainfluenzae; Hydrogenophilus thermoluteolus; Thermoanaerobacterium calidifontis; Jeotgalicoccus psychrophilus; Lactobacillus iners; Leuconostoc mesenteroides; Mesorhizobium loti; Massilia alkalitolerans; Methylobacterium extorquens; Methylobacterium gregans; Methylobacterium longum; Methylobacterium tardum; Methylobacterium thiocyanatum; Micrococcus luteus; Moraxella osloensis; Neisseria flavescens; Neisseria lactamica; Neisseria perflava; Niastella populi; Nocardiopsis composta; Nocardiopsis dassonvillei; Nocardiopsis synnemataformans; Ochrobactrum grignonense; Ochrobactrum tritici; Paenibacillus barengoltzii; Paenibacillus macerons; Paenisporosarcina quisquiliarum; Pantoea agglomerans; Paracoccus homiensis; Pelomonas puraquae; Peptostreptococcus stomatis; Petrobacter succinatimandens; Photobacterium damselae; Planomicrobium glaciei; Planomicrobium okeanokoites; Pleomorphomonas oryzae; Propionispora hippei; Pseudomonas boreopolis; Pyramidobacter piscolens; Reyranella massiliensis; Rhizobium giardinii; Rhodobacter johrii; Ruminococcus bromii; Sphingomonas paucimobilis; Sphingomonas yanoikuyae; Sporolituus thermophilus; Staphylococcus haemolyticus; Staphylococcus warneri; Stenotrophomonas maltophilia; Stenotrophomonas rhizophila; Streptococcus australis; Streptococcus cristatus; Streptococcus sanguinis; Streptococcus suis; Streptococcus thermophilus; Streptococcus tigurinus; Tepidimonas arfidensis; Tetracoccuscechii; Thermonaerobacterium aotearoense; Trichococcus pasteurii; Turicibacter sanguinis; Veillonella dispar; Veillonella montpellierensis; and Zoogloea resiniphila*.

3. A method of detecting a rosacea characteristic, the method comprising:
   (a) isolating *Demodex* mites from a biological sample of the patient;
   (b) isolating DNA from the *Demodex* mites;
   (c) using 16S rRNA gene sequencing or pyrosequencing techniques to determine the nucleic acid sequences of bacterial DNA isolated from *Demodex* mites; and
   (d) detecting an increase of the prevalence of at least one of rosacea bacteria selected from the group consisting of Firmicutes, Actinobacteria and Proteobacteria.

4. A method of detecting a rosacea characteristic, the method comprising:
   (a) isolating *Demodex* mites from a biological sample of the patient;
   (b) isolating DNA from the *Demodex* mites;
   (c) using 16S rRNA gene sequencing or pyrosequencing techniques to determine the nucleic acid sequences of bacterial DNA isolated from *Demodex* mites; and
   (d) detecting a decrease of the prevalence of the PPR bacteria, Actinobacteria, as compared to a control.

5. A method of detecting ETR bacteria in a patient suspected of rosacea, the method comprising:
   (a) isolating *Demodex* mites from a biological sample of the patient;
   (b) isolating DNA from the *Demodex* mites;
   (c) using 16S rRNA gene sequencing or pyrosequencing techniques to determine the nucleic acid sequences of bacterial DNA isolated from *Demodex* mites; and
   (d) analyzing the nucleic acid sequence of step (c) to detect one or more ETR bacteria is selected from the group consisting of *Acinetobacter schindleri, Amaricoccus kaplicensis, Anabaena augstumalis, Bartonella quintana, Dugunella zoogloeoides, Methylobacterium extorquens, Methylobacterium tardum, Neisseria flavescens, Neisseria perflava, Niastella populi, Ochrobactrum tritici, Propionispora hippei, Pseudomonas boreopolis, Pyramidobacter piscolens, Rhodobacter johrii, Sphingomonas yanoikuyae, Sporolituus thermophilus, Stenotrophomonas rhizophila, Aciditerrimonas ferrireducens, Aerococcus viridans, Anaerococcus prevotii, Bacillus frigoritolerans, Bacillus macroides, Brevibacterium album, Brevibacterium antiquum, Brevibacterium oceani, Clostridium aminovalericum, Clostridium sordellii, Corynebacterium mucifaciens, Exiguobacterium aestuarii, Gemella sanguinis, Geobacillus debilis, Geobacillus tepidamans, Jeotgalicoccus psychrophilus, Lactobacillus finers, Micrococcus luteus, Paenibacillus barengoltzii, Paenibacillus macerons, Peptostreptococcus stomatis, Planomicrobium glaciei, Streptococcus cristatus, Streptococcus thermophilus, Yeillonella dispar, Veillonella montpeffierensis, Thermoanaerobacterium calidifontis*, and *Thermoanaerobacterium aotearoense*.

6. A method of measuring an active agent's treatment effectiveness on rosacea and treating a patient in need thereof, the method comprising:
   (a) isolating *Demodex* mites from a biological sample of the patient;
   (b) isolating DNA from the *Demodex* mites;

(c) analyzing the microbiota in the biopsy based on a method of 16SrRNA sequencing or pyrosequencing;
(d) comparing the microbiota associated with *Demodex* mites from the patient before and after treating the patient; and
(e) adjusting or maintaining the treatment of the patient based on the results of step (d).

7. The method of detecting a rosacea characteristic according to claim 3, wherein the at least one rosacea bacteria is selected from the group consisting of Firmicutes and Proteobacteria.

8. A method of detecting rosacea bacteria in a patient suspected of rosacea, the method comprising:
(a) isolating *Demodex* mites from a biological sample of the patient;
(b) isolating DNA from the *Demodex* mites;
(c) using 16S rRNA gene sequencing or pyrosequencing techniques to determine the nucleic acid sequences of bacterial DNA isolated from *Demodex* mites; and
(d) analyzing the nucleic acid sequence of step (c) to detect one or more rosacea bacteria, wherein the bacteria is selected from the group consisting of *Aciditerrimonas ferrireducens; Acidovorax caeni; Acinetobacter calcoaceticus; Acinetobacter pittii; Acinetobacter schindleri; Actinomyces viscosus; Aerococcus viridans; Amaricoccus kaplicensis; Anabaena augstumalis; Anaerococcus prevotii; Anoxybacillus amylolyticus; Aquabacterium fontiphilum; Bacillus frigoritolerans; Bacillus macroides; Bartonella quintana; Brevibacterium album; Brevibacterium antiquum; Brevibacterium frigotolerans; Brevibacterium linens; Brevibacterium oceani; Clostridium aminovalericum; Clostridium celatum; Clostridium sordellii; Comamonas kersterii; Corynebacterium mucifaciens; Corynebacterium pseudogenitalium; Curvibacter delicatus; Duganella zoogloeoides; Enterobacter cloacae; Escherichia coli; Exiguobacterium aestuarii; Ferrovum myxofaciens; Friedmanniella spumicola; Gemella haemolysans; Gemella sanguinis; Geobacillus debilis; Geobacillus jurassicus; Geobacillus tepidamans; Haemophilus parainfluenzae; Hydrogenophilus thermoluteolus; Thermoanaerobacterium calidifontis; Jeotgalicoccus psychrophilus; Lactobacillus iners; Leuconostoc mesenteroides; Mesorhizobium loti; Massilia alkalitolerans; Methylobacterium extorquens; Methylobacterium gregans; Methylobacterium longum; Methylobacterium tardum; Methylobacterium thiocyanatum; Micrococcus luteus; Moraxella osloensis; Neisseria flavescens; Neisseria lactamica; Neisseria perflava; Niastella populi; Nocardiopsis cornposta; Nocardiopsis dassonvillei; Nocardiopsis synnemataformans; Ochrobactrum grignonense; Ochrobactrum tritici; Paenibacillus barengoltzii; Paenibacillus macerons; Paenisporosarcina quisquiliarum; Pantoea agglomerans; Paracoccus homiensis; Pelomonas puraquae; Peptostreptococcus stomatis; Petrobacter succinatimandens; Photobacterium damselae; Planomicrobium glaciei; Planomicrobium okeanokoites; Pleomorphomonas oryzae; Propionispora hippei; Pseudomonas boreopolis; Pyramidobacter piscolens; Reyranella massiliensis; Rhizobium giardinii; Rhodobacter johrii; Ruminococcus bromii; Sphingomonas paucimobilis; Sphingomonas yanoikuyae; Sporolituus thermophilus; Staphylococcus haemolyticus; Staphylococcus warneri; Stenotrophomonas maltophilia; Stenotrophomonas rhizophila; Streptococcus australis; Streptococcus cristatus; Streptococcus sanguinis; Streptococcus suis; Streptococcus thermophilus; Streptococcus tigurinus; Tepidimonas arfidensis; Tetracoccuscechii; Thermoanaerobacterium aotearoense; Trichococcus pasteurii; Turicibacter sanguinis; Veillonella dispar; Veillonella montpellierensis; and Zoogloea resiniphila.*

9. The method of claim 8, wherein step (c) includes one or more rosacea primer selected from the group consisting of 8F 5'-AGAGTTTGATCCTGGCTCAG-3' ("SEQ ID NOS 7"), 1510R 5'CGGTTACCTIGTTACGACTT-3' ("SEQ ID NOS 8"), and 1391R 5'-GACGGGCGGTGTGTRCA-3' ("SEQ ID NOS 9").

10. The method of claim 8, wherein the rosacea bacteria is selected from the group consisting of *Bartonella quintana* and *Escherichia coli*.

11. The method of claim 8, wherein the number of different rosacea bacteria detected are from two to five.

12. The method of claim 2, wherein the rosacea subtype is ETR and the ETR bacteria is *Bartonella*.

13. The method of claim 2, wherein the rosacea subtype is PPR and the PPR bacteria is selected from the group consisting of *Acinetobacter calcoaceticus; Acinetobacter pittii; Aquabacterium fontiphilum; Comamonas kersterii; Cundbacter delicatus; Escherichia coli; Ferrovum myxofaciens; Massilia alkalitolerans; Methylobacterium gregans; Methylobacterium thiocyanatum; Pantoea agglomerans; Paracoccus homiensis; Pelomonas puraquae; Photobacterium damselae; Pleomorphomonas oryzae; Reyranella massiliensis; Rhizobium giardinii; Sphingomonas paucimobilis; Tepidimonas arfidensis; Clostridium celatum; Friedmanniella spumicola; Geobacillus jurassicus; Leuconostoc mesenteroides; Nocardiopsis cornposta; Nocardiopsis synnemataformans; Paenisporosarcina quisquiliarum; Planomicrobium okeanokoites; Ruminococcus bromii; Staphylococcus haemolyticus; Streptococcus suis; Trichococcus pasteurii;* and *Turicibacter sanguinis.*

14. The method of claim 13 wherein the PPR bacteria is *Escherichia coli.*

15. The method of claim 2, wherein the number of different PPR bacteria detected is from two to five.

16. A method of detecting rosacea bacteria in a patient suspected of rosacea and treating rosacea in the patient, the method comprising:
(a) isolating *Demodex* mites from a biological sample of the patient;
(b) isolating DNA from the *Demodex* mites;
(c) using 16S rRNA gene sequencing or pyrosequencing techniques to determine the nucleic acid sequences of bacterial DNA isolated from *Demodex* mites;
(d) analyzing the nucleic acid sequence of step (c) to detect one or more rosacea bacteria, wherein the bacteria is selected from the group consisting of *Aciditerrimonas ferrireducens; Acidovorax caeni; Acinetobacter calcoaceticus; Acinetobacter pittii; Acinetobacter schindleri; Actinomyces viscosus; Aerococcus viridans; Amaricoccus kaplicensis; Anabaena augstumalis; Anaerococcus prevotii; Anoxybacillus amylolyticus; Aquabacterium fontiphilum; Bacillus frigoritolerans; Bacillus macroides; Bartonella quintana; Brevibacterium album; Brevibacterium antiquum; Brevibacterium frigotolerans; Brevibacterium linens; Brevibacterium oceani; Clostridium aminovalericum; Clostridium celatum; Clostridium sordellii; Comamonas kersterii; Corynebacterium mucifaciens; Corynebacterium pseudo genitalium; Curvibacter delicatus; Duganella zoogloeoides; Enterobacter cloacae; Escherichia coli; Exiguobacterium aestuarii; Ferro-* vum myxofaciens; Friedmanniella spumicola; Gemella haemolysans; Gemella sanguinis; Geobacillus debilis; Geobacillus jurassicus; Geobacillus tepidamans; Haemophilus parainfluenzae; Hydrogenophilus thermoluteolus; Thermoanaerobacterium calidifontis; Jeotgalicoccus psychrophilus; Lactobacillus iners; Leuconostoc mesenteroides; Mesorhizobium loti; Massilia alkalitolerans; Methylobacterium extorquens; Methylobacterium gregans; Methylobacterium longum; Methylobacterium tardum; Methylobacterium thiocyanatum; Micrococcus luteus; Moraxella osloensis; Neisseria flavescens; Neisseria lactamica; Neisseria perflava; Niastella populi; Nocardiopsis cornposta; Nocardiopsis dassonvillei; Nocardiopsis synnemataformans; Ochrobactrum grignonense; Ochrobactrum tritici; Paenibacillus barengoltzii; Paenibacillus macerons; Paenisporosarcina quisquiliarum; Pantoea agglomerans; Paracoccus homiensis; Pelomonas puraquae; Peptostreptococcus stomatis; Petrobacter succinatimandens; Photobacterium damselae; Planomicrobium glaciei; Planomicrobium okeanokoites; Pleomorphomonas oryzae; Propionispora hippei; Pseudomonas boreopolis; Pyramidobacter piscolens; Reyranella massiliensis; Rhizobium giardinii; Rhodobacter johrii; Ruminococcus bromii; Sphingomonas paucimobilis; Sphingomonas yanoikuyae; Sporolituus thermophilus; Staphylococcus haemolyticus; Staphylococcus warneri; Stenotrophomonas maltophilia; Stenotrophomonas rhizophila; Streptococcus australis; Streptococcus cristatus; Streptococcus sanguinis; Streptococcus suis; Streptococcus thermophilus; Streptococcus tigurinus; Tepidimonas arfidensis; Tetracoccuscechii; Thermoanaerobacterium aotearoense; Trichococcus pasteurii; Turicibacter sanguinis; Veillonella dispar; Veillonella montpellierensis; and Zoogloea resiniphila; and (e) administering an effective amount of a rosacea therapeutic to the patient when one or more rosacea bacteria is detected.

17. A method of detecting bacteria associated with rosacea subtype ETR or PPR and treating a patient suspected of rosacea, the method comprising:
   (a) isolating *Demodex* mites from a biological sample of the patient;
   (b) isolating DNA from the *Demodex* mites;
   (c) using 16S rRNA gene sequencing or pyrosequencing techniques to determine the nucleic acid sequences of bacterial DNA isolated from *Demodex* mites;
   (d) analyzing the nucleic acid sequence of step (c) to detect one or more ETR bacteria or PPR bacteria, wherein the bacteria is selected from the group consisting of *Aciditerrimonas ferrireducens; Acidovorax caeni; Acinetobacter calcoaceticus; Acinetobacter pittii; Acinetobacter schindleri; Actinomyces viscosus; Aerococcus viridans; Amaricoccus kaplicensis; Anabaena augstumalis; Anaerococcus prevotii; Anoxybacillus amylolyticus; Aquabacterium fontiphilum; Bacillus frigoritolerans; Bacillus macroides; Bartonella quintana; Brevibacterium album; Brevibacterium antiquum; Brevibacterium frigotolerans; Brevibacterium linens; Brevibacterium oceani; Clostridium aminovalericum; Clostridium celatum; Clostridium sordellii; Comamonas kersterii; Corynebacterium mucifaciens; Corynebacterium pseudogenitalium; Curvibacter delicatus; Duganella zoogloeoides; Enterobacter cloacae; Escherichia coli; Exiguobacterium aestuarii; Ferrovum myxofaciens; Friedmanniella spumicola; Gemella haemolysans; Gemella sanguinis; Geobacillus debilis; Geobacillus jurassicus; Geobacillus tepidamans; Haemophilus parainfluenzae; Hydrogenophilus thermoluteolus; Thermoanaerobacterium calidifontis; Jeotgalicoccus psychrophilus; Lactobacillus iners; Leuconostoc mesenteroides; Mesorhizobium loti; Massilia alkalitolerans; Methylobacterium extorquens; Methylobacterium gregans; Methylobacterium longum; Methylobacterium tardum; Methylobacterium thiocyanatum; Micrococcus luteus; Moraxella osloensis; Neisseria flavescens; Neisseria lactamica; Neisseria perflava; Niastella populi; Nocardiopsis cornposta; Nocardiopsis dassonvillei; Nocardiopsis synnemataformans; Ochrobactrum grignonense; Ochrobactrum tritici; Paenibacillus barengoltzii; Paenibacillus macerons; Paenisporosarcina quisquiliarum; Pantoea agglomerans; Paracoccus homiensis; Pelomonas puraquae; Peptostreptococcus stomatis; Petrobacter succinatimandens; Photobacterium damselae; Planomicrobium glaciei; Planomicrobium okeanokoites; Pleomorphomonas oryzae; Propionispora hippei; Pseudomonas boreopolis; Pyramidobacter piscolens; Reyranella massiliensis; Rhizobium giardinii; Rhodobacter johrii; Ruminococcus bromii; Sphingomonas paucimobilis; Sphingomonas yanoikuyae; Sporolituus thermophilus; Staphylococcus haemolyticus; Staphylococcus warneri; Stenotrophomonas maltophilia; Stenotrophomonas rhizophila; Streptococcus australis; Streptococcus cristatus; Streptococcus sanguinis; Streptococcus suis; Streptococcus thermophilus; Streptococcus tigurinus; Tepidimonas arfidensis; Tetracoccuscechii; Thermoanaerobacterium aotearoense; Trichococcus pasteurii; Turicibacter sanguinis; Veillonella dispar; Veillonella montpellierensis; and Zoogloea resiniphila;*

(e) administering an effective amount of a rosacea therapeutic to the patient when one or more ETR bacteria or PPR bacteria is detected.

18. A method of detecting PPR bacteria and treating a patient suspected of rosacea, the method comprising:
   (a) isolating *Demodex* mites from a biological sample of the patient;
   (b) isolating DNA from the *Demodex* mites;
   (c) using 16S rRNA gene sequencing or pyrosequencing techniques to determine the nucleic acid sequences of bacterial DNA isolated from *Demodex* mites;
   (d) analyzing the nucleic acid sequence of step (c) to detect one or more PPR bacteria, wherein the bacteria is selected from the group consisting of *Acinetobacter calcoaceticus; Acinetobacterpittir; Aquabacterium fontiphilum; Comamonas kersterii; Curvibacter delicatus; Escherichia coli; Ferrovum myxofaciens; Massilia alkalitolerans; Methylobacterium gregans; Methylobacterium thiocyanatum; Pantoea agglomerans; Paracoccus homiensis; Pelomonas puraquae; Photobacterium damselae; Pleomorphomonas oryzae; Reyranella massiliensis; Rhizobium giardinii; Sphingomonas paucimobilis; Tepidimonas arfidensis; Clostridium celatum; Friedmanniella spumicola; Geobacillus jurassicus; Leuconostoc mesenteroides; Nocardiopsis cornposta; Nocardiopsis synnemataformans; Paenisporosarcina quisquiliarum; Planomicrobium okeanokoites; Ruminococcus bromii; Staphylococcus haemolyticus; Streptococcus suis; Trichococcus pasteurii;* and *Turicibacter sanguinis;*

(e) administering an effective amount of a rosacea therapeutic to the patient when one or more PPR bacteria is detected.

19. A method of monitoring the efficacy of a rosacea therapeutic in a rosacea patient, the method comprising:
   (a) isolating *Demodex* mites from a biological sample of the patient;
   (b) isolating DNA from the *Demodex* mites;
   (c) using 16S rRNA gene sequencing or pyrosequencing techniques to determine the nucleic acid sequences of bacterial DNA isolated from *Demodex* mites;
   (d) analyzing the nucleic acid sequence of step (c) to detect one or more rosacea bacteria, wherein the rosacea bacteria is selected from the group consisting of *Aciditerrimonas ferrireducens; Acidovorax caeni; Acinetobacter calcoaceticus; Acinetobacter pittii; Acinetobacter schindleri; Actinomyces viscosus; Aerococcus viridans; Amaricoccus kaplicensis; Anabaena augstumalis; Anaerococcus prevotii; Anoxybacillus amylolyticus; Aquabacterium fontiphilum; Bacillus frigoritolerans; Bacillus macroides; Bartonella quintana; Brevibacterium album; Brevibacterium antiquum; Brevibacterium frigotolerans; Brevibacterium linens; Brevibacterium oceani; Clostridium aminovalericum; Clostridium celatum; Clostridium sordellii; Comamonas kersterii; Corynebacterium mucifaciens; Corynebacterium pseudo genitalium; Curvibacter delicatus; Duganella zoogloeoides; Enterobacter cloacae; Escherichia coli; Exiguobacterium aestuarii; Ferrovum myxofaciens; Friedmanniella spumicola; Gemella haemolysans; Gemella sanguinis; Geobacillus debilis; Geobacillus jurassicus; Geobacillus tepidamans; Haemophilus parainfluenzae; Hydrogenophilus thermoluteolus; Thermoanaerobacterium calidifontis; Jeotgalicoccus psychrophilus; Lactobacillus iners; Leuconostoc mesenteroides; Mesorhizobium loti; Massilia alkalitolerans; Methylobacterium extorquens; Methylobacterium gregans; Methylobacterium longum; Methylobacterium tardum; Methylobacterium thiocyanatum; Micrococcus luteus; Moraxella osloensis; Neisseria flavescens; Neisseria lactamica; Neisseria perflava; Niastella populi; Nocardiopsis cornposta; Nocardiopsis dassonvillei; Nocardiopsis synnemataformans; Ochrobactrum grignonense; Ochrobactrum tritici; Paenibacillus barengoltzii; Paenibacillus macerons; Paenisporosarcina quisquiliarum; Pantoea agglomerans; Paracoccus homiensis; Pelomonas puraquae; Peptostreptococcus stomatis; Petrobacter succinatimandens; Photobacterium damselae; Planomicrobium glaciei; Planomicrobium okeanokoites; Pleomorphomonas oryzae; Propionispora hippei; Pseudomonas boreopolis; Pyramidobacter piscolens; Reyranella massiliensis; Rhizobium giardinii; Rhodobacter johrii; Ruminococcus bromii; Sphingomonas paucimobilis; Sphingomonas yanoikuyae; Sporolituus thermophilus; Staphylococcus haemolyticus; Staphylococcus warneri; Stenotrophomonas maltophilia; Stenotrophomonas rhizophila; Streptococcus australis; Streptococcus cristatus; Streptococcus sanguinis; Streptococcus suis; Streptococcus thermophilus; Streptococcus tigurinus; Tepidimonas arfidensis; Tetracoccuscechii; Thermoanaerobacterium aotearoense; Trichococcus pasteurii; Turicibacter sanguinis; Veillonella dispar; Veillonella montpellierensis;* and *Zoogloea resiniphila;*
   (e) administering an effective amount of a rosacea therapeutic to the patient;
   (g) repeating steps (a)-(d);
   (h) comparing the rosacea bacteria profile of the patient to that of a control; and
   (i) repeating steps (e)-(g) until the rosacea bacteria profile of the patient is comparable to that of the control.

20. The method of claim 19, wherein the control is a biological sample from a healthy patient.

* * * * *

SEQUENCE LISTING

<160> NUMBER OF SEQ ID NOS: 11

<210> SEQ ID NO 1
<211> LENGTH: 26
<212> TYPE: DNA
<213> ORGANISM: artificial sequence
<220> FEATURE:
<223> OTHER INFORMATION: Probe

<400> SEQUENCE: 1
tgggttgatt gacaaacgct tttgag          26

<210> SEQ ID NO 2
<211> LENGTH: 20
<212> TYPE: DNA
<213> ORGANISM: artificial sequence
<220> FEATURE:
<223> OTHER INFORMATION: Primer

<400> SEQUENCE: 2
caaaagcccg taagaagcac          20

<210> SEQ ID NO 3
<211> LENGTH: 20
<212> TYPE: DNA
<213> ORGANISM: artificial sequence
<220> FEATURE:
<223> OTHER INFORMATION: Primer

<400> SEQUENCE: 3
attggccttc gcctttactt          20

<210> SEQ ID NO 4
<211> LENGTH: 17
<212> TYPE: DNA
<213> ORGANISM: artificial sequence
<220> FEATURE:
<223> OTHER INFORMATION: Probe

<400> SEQUENCE: 4
cgtcrtcccc rccttcc          17

<210> SEQ ID NO 5
<211> LENGTH: 17
<212> TYPE: DNA
<213> ORGANISM: artificial sequence
<220> FEATURE:
<223> OTHER INFORMATION: Primer

```
<400> SEQUENCE: 5
gacgggcggt gtgtrca                                                  17

<210> SEQ ID NO 6
<211> LENGTH: 16
<212> TYPE: DNA
<213> ORGANISM: artificial sequence
<220> FEATURE:
<223> OTHER INFORMATION: Primer

<400> SEQUENCE: 6
gyaacgagcg caaccc                                                   16

<210> SEQ ID NO 7
<211> LENGTH: 20
<212> TYPE: DNA
<213> ORGANISM: artificial sequence
<220> FEATURE:
<223> OTHER INFORMATION: Primer

<400> SEQUENCE: 7
agagtttgat cctggctcag                                               20

<210> SEQ ID NO 8
<211> LENGTH: 20
<212> TYPE: DNA
<213> ORGANISM: artificial sequence
<220> FEATURE:
<223> OTHER INFORMATION: Primer

<400> SEQUENCE: 8
cggttacctt gttacgactt                                               20

<210> SEQ ID NO 9
<211> LENGTH: 17
<212> TYPE: DNA
<213> ORGANISM: artificial sequence
<220> FEATURE:
<223> OTHER INFORMATION: Primer

<400> SEQUENCE: 9
gacgggcggt gtgtrca                                                  17

<210> SEQ ID NO 10
<211> LENGTH: 24
<212> TYPE: DNA
<213> ORGANISM: artificial sequence
<220> FEATURE:
<223> OTHER INFORMATION: Primer

<400> SEQUENCE: 10
cgccagggtt ttcccagtca cgac                                          24

<210> SEQ ID NO 11
<211> LENGTH: 21
<212> TYPE: DNA
<213> ORGANISM: artificial sequence
<220> FEATURE:
<223> OTHER INFORMATION: Primer

<400> SEQUENCE: 11
tcacacagga aacagctatg a                                             21
```